US009549946B2

(12) United States Patent
Alverdy

(10) Patent No.: US 9,549,946 B2
(45) Date of Patent: Jan. 24, 2017

(54) MATERIALS AND METHODS FOR PREVENTING AND TREATING MICROBE-MEDIATED EPITHELIAL DISORDERS

(71) Applicant: THE UNIVERSITY OF CHICAGO, Chicago, IL (US)

(72) Inventor: John C. Alverdy, Glenview, IL (US)

(73) Assignee: THE UNIVERSITY OF CHICAGO, Chicago, IL (US)

(*) Notice: Subject to any disclaimer, the term of this patent is extended or adjusted under 35 U.S.C. 154(b) by 0 days.

(21) Appl. No.: 14/936,088

(22) Filed: Nov. 9, 2015

(65) Prior Publication Data

US 2016/0129038 A1 May 12, 2016

Related U.S. Application Data

(63) Continuation of application No. 10/535,918, filed as application No. PCT/US02/37948 on Nov. 26, 2002, now abandoned.

(51) Int. Cl.

| | | |
|---|---|---|
| *A61K 31/765* | (2006.01) | |
| *A23K 20/105* | (2016.01) | |
| *A23K 50/20* | (2016.01) | |
| *A23K 50/10* | (2016.01) | |
| *A23K 50/75* | (2016.01) | |
| *A23K 50/30* | (2016.01) | |
| *A23K 50/40* | (2016.01) | |
| *A61K 31/198* | (2006.01) | |
| *A61K 31/721* | (2006.01) | |
| *A23L 33/00* | (2016.01) | |
| *A23L 33/10* | (2016.01) | |

(52) U.S. Cl.
CPC ............ *A61K 31/765* (2013.01); *A23K 20/105* (2016.05); *A23K 50/10* (2016.05); *A23K 50/20* (2016.05); *A23K 50/30* (2016.05); *A23K 50/40* (2016.05); *A23K 50/75* (2016.05); *A23L 33/10* (2016.08); *A23L 33/40* (2016.08); *A61K 31/198* (2013.01); *A61K 31/721* (2013.01)

(58) Field of Classification Search
None
See application file for complete search history.

(56) References Cited

U.S. PATENT DOCUMENTS

| | | | |
|---|---|---|---|
| 3,487,150 A * | 12/1969 | Redo | A61K 31/715 514/59 |
| 3,817,837 A | 6/1974 | Rubenstein et al. | |
| 3,850,752 A | 11/1974 | Schuurs et al. | |
| 3,939,350 A | 2/1976 | Kronick et al. | |
| 3,996,345 A | 12/1976 | Ullman et al. | |
| 4,277,437 A | 7/1981 | Maggio | |
| 4,659,572 A * | 4/1987 | Murray | A61L 15/225 424/448 |
| 4,837,008 A | 6/1989 | Rudy et al. | |
| 5,169,627 A | 12/1992 | Cunningham-Rundles | |
| H1198 H | 6/1993 | Larrick et al. | |
| 5,350,770 A | 9/1994 | Elford et al. | |
| 5,409,903 A | 4/1995 | Polak et al. | |
| 5,661,177 A | 8/1997 | Blum et al. | |
| 5,662,905 A | 9/1997 | Siadak et al. | |
| 5,942,237 A | 8/1999 | Gizurarson et al. | |
| 6,017,334 A | 1/2000 | Rawls | |
| 6,074,671 A | 6/2000 | Oldham et al. | |
| 6,126,933 A | 10/2000 | Warne et al. | |
| 6,321,909 B1 * | 11/2001 | Wicomb | A01N 1/02 206/438 |
| 6,329,391 B1 | 12/2001 | Ledoussal et al. | |
| 6,733,781 B2 | 5/2004 | Abu-Izza et al. | |

FOREIGN PATENT DOCUMENTS

| | | |
|---|---|---|
| CN | 1088432 A | 6/1994 |
| CN | 1491676 A | 4/2004 |
| EP | 0295009 A2 | 12/1988 |
| RU | 2035913 C1 | 5/1995 |

(Continued)

OTHER PUBLICATIONS

Yu et al. Zhonghua wa ke za zhi. 1995, 33(12):742-744.*
Adam, "Bacteria get the brush off", *Nature*, 2 pages [online] (2000).
Ahdieh et al., Lung epithelial barrier function and wound healing are decreased by IL-4 and IL-13 and enhanced by IFN-gamma. *AJP Cell Physiol*. 281: C2029-38 (2001).
Alverdy et al., "Gut-Derived Sepsis Occurs When the Right Pathogen with the Right Virulence Genes Meets with Right Host," Annals of Surgery, 232:480-489 (2000).
Alverdy, et al. "Whole gut washout for severe sepsis: Review of techynique and preliminary results," Surgery 121(1):89-94 (1997).
Ammori et al., Early increase in intestinal permeability in patients with severe acute pancreatitis: Correlation with endotoxemia, organ failure, and mortality. *J. Gastrointestinal Surg*. 3(3): 252-62 (1999).
Avichezer et al., Analysis of the amino acid sequence of the *Pseudomonas aeruginosa* galactophilic PA-I lectin. *J. Biol. Chem*. 267(32): 23023-7 (1992).

(Continued)

*Primary Examiner* — Oluwatosin Ogunbiyi
(74) *Attorney, Agent, or Firm* — Marshall, Gerstein & Borun LLP

(57) ABSTRACT

The present invention provides pharmaceutical compositions in the form of relatively high molecular weight biocompatible polymers such as polyethylene glycol, optionally supplemented with a protective polymer such as dextran and/or essential pathogen nutrients such as L-glutamine. Also provided are methods for preventing or treating gut-derived sepsis attributable to intestinal pathogens such as *Pseudomonas aeruginosa* by administering high molecular weight polyethylene glycol as well as methods for monitoring the administration of high molecular weight polyethylene glycol, such as in methods of preventing, ameliorating or treating microbe-induced epithelial disorders, as exemplified by gut-derived sepsis. Frequently, gut-derived sepsis arises as a complication in mammals recovering from surgical intervention or suffering from a disease or disorder, providing indications of suitable animals to receive preventative treatment. Finally, the invention provides a composition comprising infant formula and polyethylene glycol and methods for using that composition.

20 Claims, 6 Drawing Sheets

(56) References Cited

FOREIGN PATENT DOCUMENTS

| WO | WO-94/02135 | 2/1994 |
|---|---|---|
| WO | WO-98/54982 A1 | 12/1998 |
| WO | WO-99/08514 | 2/1999 |
| WO | WO-99/39732 A1 | 8/1999 |
| WO | WO-01/12222 A1 | 2/2001 |
| WO | WO-01/17560 | 3/2001 |

OTHER PUBLICATIONS

Avichezer et al., Pseudomonas aeruginosa PA-I lectin gene molecular analysis and expression in Escherichia coli. Biochimica Biophysica Acta. 1218: 11-20 (1994).
Bajolet-Laudinat et al., "Cytotoxicity of Pseudomonas aeruginosa Internal Lectin PA-I to Respiratory Epithelial Cells in Primary Culture," Infection and Immunity 62(10):4481-4487 Abstract (1994).
Blackall, et al. "Polyethylene glycol-coated red blood cells fail to bind glycophorin A-specific antibodies and are impervious to invastion by the Plasmodium falciparum malaria parasite," Blood 97(2):551-556 (2001).
Chapman et al. "Polymeric thin films that resist the adsorption of proteins and the adhesion of bacteria", Langmuir, 17:1225-33 (2001).
Chirfe et al., Invitro antibacterial activity of concentrated polyethylene glycol 400 solution. Antimicrob. Agents Chremother. 24(3): 409-14 (1983).
Cisneros, et al., "Passive Transfer of Poly-(1-6)-β-Glucotriosyl-(1-3)-β-Glucopyranose Glucan Protection against Lethal Infection in an Animal Model of Intra-Abdominal Sepsis," Infection and Immunity, 64(6):2201-2205 (1996).
Corpet et al., "Polyethylene-glycol, a potent suppressor of azoxymethane-induced colonic aberrant crypt foci in rats," Carcinogenesis 20(5):915-918 (1999).
Cox "Bacterial Survival in Suspension in Polyethylene Glycol Solutions," J. Gen. Microbiol. 45:275-281 (1966).
Cryz, et al. "Protection against Pseudomonas aeruginosa infection in a murine burn wound sepsis model by passive transfer of antitoxin A, antielastase, and antilipopolysaccharide," Infect Immun 39(3):1072-9 (1983).
del Cacho et al., Expression of flotillin-1 of Emeria tenella sporozoites and its role in host cell invastion. J. Parasitol. 93(2):328-32 (2007).
Desai et al., Solution technique to incorporate polyethylene oxide and other water-soluble polymers into surfaces of polymeric biomaterials. Biomaterials, 12: 144-53 (1991).
Desai eta l., Surface-immobilized polyethylene oxide bacterial repellence. Biomaterials, 13(7): 417-20 (1992).
Espat et al., PEG-BP-30 monotherapy attenuates the cytokine-mediated inflammatory cascade in baboon Escherichia coli septic shock. J. Surg. Res. 59(1): 153-8 (1995).
Faure, et al. "Polyethylene Glycol Reduces Early and Long-Term Cold Ischemia-Reperfusion and Renal Medulla Injury," The Journal of Pharmacology and Experimental Therapetics 302(3):861-870 (2002).
Feltis et al., Does microbial translocation play a role in critical illness? Curr. Opin Crit. Care, 6: 117-22 (2000).
Garber et al., On the specificity of the D-galactose-binding lectin (PA-I) of Pseudomonas aeruginosa and its strong binding to hydrophobic derivatives of D-galactose and thiogalactose. Biochem. Biophys. Acta. 1116(3): 331-3 (1992) ABSTRACT.
Glick et al., The intracellular localization of Pseudomonas aeruginosa Lectins. J. General Microbiol. 129: 3085-90 (1983).
International Search Report for PCT/US2002/37948, dated Feb. 23, 2003.
Itasaka et al., Modification of reject by polyethylene glycol in small bowel transplantation. Transplantation, 57(5): 646-8 (1994).
Kelleher et al., "Supplementation of Infant Formula With the Probiotic Lactobacillus reuteri and Zinc: Impact on Enteric Infection and Nutrition in Infant Thesus Monkeys," Journal of Pediatric Gastroentrology and Nutrition, 35:162-168 (2002).
Lanne et al., Binding of the galactose-specific Pseudomonas aeruginosa lectin, PA-I, to glycosphingolipids and other glycoconjugates. Glycocoj. J. 11(4): 292-8 (1994) ABSTRACT.
Laughlin et al., The key role of Pseudomonas aeruginosa PA-I lectin on experimental gut-derived sepsis. Ann. Surg. (1): 133-42 (2000).
Majtan et al., Toxinogenicity and markers of pathogenicity of Pseudomonas aeroginosa strains isolated from patients with tumor disease. Folia Microbiol. 47: 445-9 (2002).
Matsumoto et al., Effect of immunization with Pseudomonas aeruginosa on gut-derived sepsis in mice. J. Med. Microbiol. 47: 295-301 (1998).
Matsumoto et al., Effect of passive immunotherapy on murine gut-derived sepsis caused by Pseudomonas aeruginosa. J. Med. Microbiol. 48: 765-70 (1999).
Matsumoto et al., Efficacies of alkaline protease, elastase and exotoxin A toxoid vaccines against gut-derived Pseudomonas aeruginosa sepsis in mice. J. Med. Microbiol. 47: 303-8 (1998).
Naigamwalla, et al., "Polyethylene Glycol 8000 and Colon Carcinogenesis: Inhibition in the F344 Rat, Promotion in the Min Mouse," Cancer Research 60:6856-6858 (2000).
Opal et al. "Potential hazards of combination immunotherapy in the treatment of experimental septic shock", J. Infect. Dis. 173:1415-21 (1996).
Osada et al., Effect of L18-MDP(Ala), a synthetic derivative of muramyl dipeptide, on nonspecific resistance of mice to microbial infections. Infect. Immun. 37(1): 292-300 (1982).
Parnaud et al., Polyethylene-glycol suppresses colon cancer and causes dose-dependent regression of azoxymethane-induced aberrant crypt foci in rats. Cancer Res. 59: 5143-7 (1999).
Roy et al., Polyethylene glycol induces apoptosis in HT-29 cells: Potential mechanism for chemoprevention of colon cancer. FEBS Lett. 496: 143-6 (2001).
Shi et al., Mucin coating on polymeric material surfaces to suppress bacterial adhension. Colloids Surfaces. B. Biointerfaces, 17: 229-39 (2000).
Somack et al. "Preparation of long-acting superoxide dismutase using high molecular weight polyethylene glycol," Free Radic Res Commun, 2:553-62 (1991), abstract.
Sordillo, et al. "Morphological study of chronic Staphylococcus aureus mastitis in the lactating bovine mammary gland," Research in Veterinary Science 47(2):247-252 (1989).
Spitz et al., Characteristics of the intestinal epithelial barrier during dietary manipulation and glucocorticoid stress. Crit. Care Med. 24: 635-41 (1996).
Supplemental European Search Report for EP-02 78 9898, dated Apr. 9, 2009.
Tissue Engineering and Artificial Organs, Edited by Joseph D. Brozino, 34d edition, p. 2-5 to 2-6 (2006).
Ukuku et al., Relationship of cell surface charge and hydrophobicity to strength of attachment of bacteria to cantaloupe rind. J. Food Prot. 65: 1093-9 (2002).
Van Delden et al., Cell-to-cell signaling and Pseudomonas aeruginosa infections. Emerg. Infect. Dis. 4(4): 551-60 (1998).
Walker, et al. "Evaluation of Pseudomonas aeruginosa toxin A in experimental rat burn wound sepsis," Infect Immun 25(3):828-30 (1979).
Winzer et al., The Pseudomonas aeruginosa lectins PA-IL and PA-IIL are controlled by quorum sensing and by RpoS. J. Bacteriol. 6401-11 (2000).

\* cited by examiner

MATERIALS AND METHODS FOR PREVENTING AND TREATING MICROBE-MEDIATED EPITHELIAL DISORDERS

CROSS-REFERENCE TO RELATED APPLICATIONS

This application is a Continuation of U.S. application Ser. No. 10/535,918, filed Mar. 16, 2006, which is a U.S. National Phase of PCT/US2002/37948, filed Nov. 26, 2002, the disclosures of which are incorporated herein by reference in their entirety.

FIELD OF INVENTION

The present invention relates to materials and methods for preventing or treating microbe-mediated epithelial disorders, such as gut-derived sepsis.

BACKGROUND

Microbe-mediated epithelial disorders, or abnormal conditions, present a significant threat to the health of man and animals, imposing a burden on healthcare systems worldwide. One example of such disorders, gut-derived sepsis, is a major cause of mortality among organisms, such as human patients, that suffer from any of a variety of diseases, disorders or afflictions, such as burn injuries, neonatal enterocolitis, severe neutropenia, inflammatory bowel disease, and organ rejection following transplantation. The intestinal tract reservoir has long been recognized to be a potentially lethal focus of bacterial-mediated sepsis in, e.g., critically ill, hospitalized patients. The ability of microbial pathogens such as the Pseudomonads (e.g., *Pseudomonas aeruginosa*) to perturb the regulatory function of the intestinal epithelial barrier may be a defining characteristic among opportunistic organisms capable of causing gut-derived sepsis. In many of these infections, *Pseudomonas aeruginosa* has been identified as the causative pathogen. Significantly, the intestinal tract has been shown to be the primary site of colonization of opportunistic pathogens such as *P. aeruginosa*.

Conventional therapeutic approaches to the prevention or treatment of microbe-mediated epithelial disorders such as gut-derived sepsis have met with incomplete success. Antibiotic-based approaches are compromised by the difficulty in tailoring antibiotics to the intestinal pathogen in a manner that does not impact the remaining intestinal flora. In addition, many of the intestinal pathogens, as typified by *P. aeruginosa*, often become resistant to antibiotic challenges, resulting in a costly, ongoing and incompletely successful approach to prevention or treatment. Problems also plague immunotherapeutic approaches. Particularly, many intestinal pathogens such as *P. aeruginosa*, are immunoevasive, rendering such approaches minimally effective.

Another approach to the prevention or treatment disorders such as gut-derived sepsis is intestinal lavage. In the past several years, intestinal lavage using polyethylene glycol (PEG) solutions has been attempted, with some anecdotal reports suggesting that PEG may show some promise in treating gut-derived sepsis across a variety of clinical and experimental circumstances. The PEG in these solutions has an average molecular weight of 3,500 daltons and the solutions are commercially available (e.g., Golytely). The mechanisms by which these relatively low molecular weight (LMW) solutions of PEG provide a therapeutic benefit in treating or preventing gut-derived sepsis is unknown. Typically, these solutions are used to wash or flush the intestinal tract of organisms at risk of developing, or suffering from, gut-derived sepsis. As a result of administering these LMW PEG solutions to the intestinal tract, there is a variable change in the floral composition of the treated intestine depending on the method of concentration and the molecular weight of the compounds used. For example, solutions having concentrations of PEG higher than about 20% can result in a microbiocidal action resulting in the elimination of potentially protective microorganisms in the intestinal tract of a stressed host. Also, solutions of low molecular weight PEG can lose their efficacy in attenuating the virulence capacity of certain organisms, despite preserving them. Therefore, a need exists in the art for a solution that inhibits microbial virulence expression (the harmful properties of a microbe) while not killing the microbe or neighboring microbes, thereby providing the benefit of preserving the natural ecosystem of the intestinal microflora. For example, preservation of the native floral composition would provide competition for opportunistic pathogens that might otherwise colonize the intestine.

Concomitant with a change in floral composition is a change in the physiology of the organism. These physiological changes may be monitored by assaying any number of characteristic enzymatic activities, such as lactate dehydrogenase levels. Consequently, LMW PEG treatments of the intestine produce significant changes in the physiology of the treated organisms, with unpredictable, and thus potentially deleterious, longer-term consequences for the health and well-being of the treated organism. Moreover, such treatments provoke physically demanding reactions in the form of massive intestinal voiding in critically ill organisms such as hospitalized human patients.

Thus, there remains a need in the art to provide a composition effective in preventing, or treating, a microbe-mediated epithelial disorder (e.g., gut-derived sepsis) and/or a symptom associated with such a disorder, along with methods for achieving such benefits, without creating the potential for further complications through significant alteration of the physiology of the treated organism.

SUMMARY OF THE INVENTION

The present invention satisfies the aforementioned need in the art by providing a high molecular weight (HMW) polyethylene glycol composition that provides effective protection against an abnormal condition characterized by an epithelial surface at risk of developing a microbe-mediated disorder. Exemplary abnormal conditions include gut-derived sepsis, and other intestinal disorders/diseases associated with intestinal flora, due to intestinal pathogens including, but not limited to, *P. aeruginosa*. The HMW PEG inhibits or prevents contact of such pathogens as *P. aeruginosa* with the intestinal epithelial surface. In addition, high molecular weight PEG suppresses virulence expression in these pathogens (e.g., *P. aeruginosa*) responsive to a variety of signals that may involve quorum sensing signaling networks. The ability of HMW PEGs to interdict at the infectious interface between the intestinal pathogen and the intestinal epithelium provides an alternative approach to preventing or treating gut-derived sepsis, e.g., following catabolic stress. Importantly, treatments with HMW PEGs would be cost effective and relatively simple to perform on human patients as well as a variety of other organisms such as agriculturally significant livestock (e.g., cattle, pigs, sheep, goats, horses, chickens, turkeys, ducks, geese, and the like), pets, and zoo animals.

One aspect of the invention provides a method of reducing the likelihood of mortality in an animal with an abnormal condition, including a disease condition, comprising an epithelial surface at risk of developing a microbe-mediated disorder selected from the group consisting of gut-derived sepsis, a burn injury, neonatal necrotizing enterocolitis, severe neutropenia, toxic colitis, inflammatory bowel disease, enteropathy, transplant rejection, pouchitis, and pig belly, comprising administering an effective dose of polyethylene glycol (PEG) to an animal in need thereof, wherein the PEG has an average molecular weight of at least 5,000 daltons. Suitable animals include, but are not limited to, dog, cat, sheep, goat, cow, pig and human. In the aforementioned method, the PEG preferably has an average molecular weight of at least 15,000 daltons, and is preferably between 5,000 and 20,000 daltons, or between 15,000 and 20,000 daltons. Also preferred is PEG having an average molecular weight of 6,000, of 7,000, of 8,000, of 9,000, of 10,000, of 11,000, of 12,000 of 13,000, of 14,000, and of 25,000 daltons. Further, the PEG may be in an aqueous solution comprising 5-20% PEG, and preferably 10-20% PEG (e.g., 10% PEG). In one embodiment of the method, the condition is associated with the presence of a *Pseudomonas aeruginosa* organism in the intestine and the cell membrane integrity of such *P. aeruginosa* is not detectably altered. In another embodiment of the method, the growth pattern of *Pseudomonas aeruginosa* is not detectably altered.

Another aspect of the invention is a method of inhibiting gut-derived sepsis comprising contacting a mammalian epithelium, such as an intestine, with polyethylene glycol (PEG), wherein the PEG has an average molecular weight of at least 5,000 daltons, and preferably at least 15,000 daltons. In one embodiment of this method, the mammalian intestine contacts the PEG for at least 30 minutes.

Further aspects of the invention include a method of inhibiting PA-I lectin/adhesin expression in a pathogen of the epithelia, e.g., an intestinal pathogen, comprising administering an effective dose of polyethylene glycol to an animal in need thereof; a method of inhibiting epithelium-induced (e.g., intestinal epithelium-induced) activation of PA-I lectin/adhesin comprising administering an effective dose of polyethylene glycol to an animal in need thereof; a method of inhibiting C4-HSL-induced morphological change of a pathogen of the epithelia (e.g., an intestinal pathogen) comprising administering an effective dose of polyethylene glycol to an animal in need thereof; a method of reducing virulence expression in a pathogen of the epithelia (e.g., an intestinal pathogen) comprising administering an effective dose of polyethylene glycol to an animal in need thereof; a method of reducing or preventing interaction of an epithelial surface with a microbial virulence factor comprising administering an effective dose of polyethylene glycol to an animal in need thereof; a method of ameliorating epithelial (e.g., intestinal) pathogenesis by preventing formation of pathogenic quorum-sensing activation comprising administering an effective dose of polyethylene glycol to an animal in need thereof; and a method of inhibiting interaction between epithelium (e.g., intestinal epithelium) of a vertebrate and a bacterium, such as a Pseudomonad (e.g., *Pseudomonas aeruginosa*), comprising contacting the epithelium with polyethylene glycol. In all of these aspects of the invention, the PEG has an average molecular weight of at least 5,000 daltons, and preferably at least 15,000 daltons.

A still further aspect of the invention is a method of inhibiting a *Pseudomonas aeruginosa*-induced reduction in the transepithelial electrical resistance of a mammalian epithelial layer, such as an intestinal epithelial layer, comprising contacting the (intestinal) epithelial layer with polyethylene glycol, wherein the PEG has an average molecular weight of at least 5,000 daltons, and preferably at least 15,000 daltons. Preferably, the PEG has an average molecular weight of 15,000 to 20,000 daltons. In a preferred embodiment, the integrity of the membrane of the microbe (e.g., *P. aeruginosa*) is not detectably altered.

Yet another aspect of the invention is a method of inhibiting adherence of a bacterial cell to a mammalian epithelium, such as a mammalian intestine, comprising contacting the intestine with polyethylene glycol, wherein the PEG has an average molecular weight of at least 5,000 daltons, and preferably at least 15,000 daltons. With this method as well, it is preferred that the PEG has an average molecular weight of 15,000 to 20,000 daltons. The PEG may be in an aqueous solution comprising 5-20% PEG, and preferably 5-10% PEG. An exemplary bacterial cell contemplated as amenable to inhibition of adherence by this method is a Pseudomonad, such as *P. aeruginosa*.

Another aspect of the invention is a method of reducing the expression of PA-I lectin/adhesin in a bacterial cell comprising contacting the bacterial cell with polyethylene glycol, wherein the PEG has an average molecular weight of at least 5,000 daltons, and preferably 15,000 daltons, and is preferably between 15,000 and 20,000 daltons. Again, the PEG may be in an aqueous solution comprising 5-20% PEG, and preferably 5-10% PEG.

In another aspect, the invention provides a method of reducing the likelihood of mortality in an animal exhibiting a microbe-mediated epithelial disorder selected from the group consisting of gut-derived sepsis, a burn injury, neonatal necrotizing enterocolitis (NEC), severe neutropenia, toxic colitis, inflammatory bowel disease, enteropathy (e.g., in the critically ill), transplant rejection, pouchitis and pig belly comprising administering an effective amount of a compound (e.g., PEG) that adheres to a cell selected from the group consisting of a mammalian intestinal epithelial cell and an intestinal bacterial cell, wherein the compound adheres to the cell in a topographically asymmetrical manner, thereby inhibiting interaction of the mammalian intestinal epithelial cell and the bacterial cell. A preferred compound is a surfactant. In one embodiment of this method, the compound is PEG, preferably having an average molecular weight of at least 15,000 daltons. In another embodiment of this method, the inhibition is determined by atomic force microscopy. In yet another embodiment of this method, the bacterial cell is an intestinal pathogen and there is no detectable modification of its growth characteristics. In related aspects, this method further comprises introducing an effective amount of dextran into the intestine of the animal and/or introducing an effective amount of L-glutamine, dextran-coated L-glutamine, dextran-coated inulin, dextran-coated butyric acid, one or more fructo-oligosaccharides, N-acetyl-D-galactosamine, dextran-coated mannose and galactose, lactulose and balancing buffers and stabilizing agents, known in the art, into the intestine of the animal. When administered together as a single composition, this multicomponent single-solution administration will treat and prepare the intestinal tract in anticipation of a disruption in the intestinal flora and barrier function of the intestine, such as occurs following severe catabolic-, surgical- and traumatic-type stresses.

Another aspect of the invention is a method of ameliorating a symptom associated with any disease or condition arising from, or characteristic of, an abnormal condition of the epithelium, such as gut-derived sepsis, comprising administering polyethylene glycol to the intestine, wherein the PEG has an average molecular weight of at least 5,000 daltons, preferably at least 15,000 daltons, and is preferably between 15,000 and 20,000 daltons. The PEG may be in an aqueous solution comprising 5-20% PEG, and preferably 5-10% PEG. The invention comprehends ameliorating a symptom associated with any disease or condition disclosed herein.

Still another aspect of the invention is a method of preventing loss of lactating capacity in an animal exhibiting an abnormal condition in the form of an epithelial surface of a mammary gland at risk of developing a microbe-mediated disorder affecting milk output, comprising administering, e.g., topically, an effective dose of a polyethylene glycol of at least 5,000 daltons, and preferably at least 15,000 daltons, to the epithelial surface of a mammary gland. Exemplary animals include mammals, such as sheep, goats, cows, pigs, horses and humans. In a related aspect, the invention provides a method of treating a loss of lactating capacity in an animal characterized by a microbe-mediated disorder of an epithelial surface of a mammary gland affecting milk output, comprising administering, e.g., topically, an effective dose of a polyethylene glycol of at least 5,000 daltons and, preferably, at least 15,000 daltons to a mammary gland. In another related aspect, the invention provides a method of preventing development of a microbe-mediated epithelial disorder in an animal of nursing age comprising administering an effective dose of polyethylene glycol of at least 5,000 daltons, and preferably at least 15,000 daltons, to the animal. Suitable animals include mammals, such as humans, livestock, domesticated pets, and zoo animals. In one embodiment, the PEG is admixed with any infant formula known in the art.

A related aspect of the invention is a composition comprising infant formula and polyethylene glycol (PEG), wherein the PEG has an average molecular weight of at least 5,000 daltons. Again, any infant formula known in the art may be used, including formulas based on the milk of a mammal, such as cow's milk, goat's milk, and the like, as well as formulas based on soy milk. The formula may also be enriched with any vitamin and/or element, including fortification with iron. The PEG preferably has an average molecular weight of at least 15,000 daltons, and is preferably present in the range of 5-20% upon reconstitution or hydration of the infant or baby formula. The invention further provides a method of providing nutrition to an animal, preferably of nursing age, comprising administering an effective dose of the composition comprising infant formula and PEG to the animal.

Yet another aspect of the invention is a pharmaceutical composition comprising polyethylene glycol of at least 5,000 daltons, and preferably 15,000 daltons, average molecular weight and a suitable adjuvant, carrier or diluent. In a related aspect, the composition further comprises a compound selected from the group consisting of dextran-coated L-glutamine, dextran-coated inulin, dextran-coated butyric acid, one or more fructo-oligosaccharides, N-acetyl-D-galactosamine, dextran-coated mannose and galactose, lactulose and balancing buffers and stabilizing agents known in the art.

An additional aspect of the invention is a kit for the therapeutic treatment or prevention of an abnormal condition characterized by an epithelial surface at risk of developing a microbial-mediated disorder, such as gut-derived sepsis, comprising one of the above-described pharmaceutical compositions and a protocol describing use of the composition in therapeutic treatment or prevention of the abnormal condition. Protocols suitable for inclusion in the kit describe any one of the therapeutic or preventive methods disclosed herein.

Still other aspects of the invention are drawn to methods of preventing an abnormal condition characterized by an epithelial surface at risk of microbe-mediated disorder, including diseases. For example, the invention comprehends a method of preventing a disease or an abnormal condition comprising administering a composition comprising an effective dose of polyethylene glycol (PEG) to an animal, wherein the PEG has an average molecular weight of at least 5,000 daltons. A suitable disease or abnormal condition, amenable to the preventive methods of the invention, is selected from the group consisting of swimmer's ear, acute otitis media, chronic otitis media, ventilator-associated pneumonia, gut-derived sepsis, necrotizing enterocolitis, antibiotic-induced diarrhea, pseudomembranous colitis, an inflammatory bowel disease, irritable bowel disease, neutropenic enterocolitis, pancreatitis, chronic fatigue syndrome, dysbiosis syndrome, microscopic colitis, a chronic urinary tract infection, a sexually transmitted disease, and infection. An animal suitable as a subject for such preventive methods is selected from the group consisting of dog, cat, sheep, goat, cow, pig, chicken, horse and human. The PEG preferably has an average molecular weight of at least 15,000 daltons; also preferred is PEG having an average molecular weight between 15,000 and 20,000 daltons. Further, the PEG may be an aqueous solution comprising 10-20% PEG, and preferably 10% PEG. The composition being administered may further comprise a vehicle selected from the group consisting of a liquid solution, a topical gel, and a solution suitable for nebulizing. Additionally, the composition may further comprise a compound selected from the group consisting of dextran-coated L-glutamine, dextran-coated inulin, dextran-coated butyric acid, a fructo-oligosaccharide, N-acetyl-D-galactosamine, dextran-coated mannose, galactose and lactulose. In one embodiment, the composition comprises PEG, dextran-coated L-glutamine, dextran-coated inulin, dextran-coated butyric acid, a fructo-oligosaccharide, N-acetyl-D-galactosamine, dextran-coated mannose, galactose and lactulose.

Yet another aspect of the invention is a method of preventing skin infection comprising the step of applying a composition comprising an effective amount of polyethylene glycol (PEG) to an animal, wherein the PEG has an average molecular weight of at least 5,000 daltons. The composition may further comprise a vehicle selected from the group consisting of an ointment, a cream, a gel and a lotion. The invention contemplates that an agent causing the infection is selected from the group consisting of *Bacillus anthracis*, Small Pox Virus, enteropathogenic *E. coli* (EPEC), enterohemorrhagic *E. coli* (EHEC), enteroaggregative *E. coli*, (EAEC), *Clostridium difficile*, rotavirus, *Pseudomonas aeruginosa, Serratia marcescens, Klebsiella oxytocia, Enterobacteria cloacae, Candida albicans* and *Candida globrata*.

Another aspect of the invention is a method of preventing respiratory infection comprising the step of administering an effective amount of polyethylene glycol (PEG) to an animal, wherein the PEG has an average molecular weight of at least 5,000 daltons. A respiratory infection amenable to the preventive methods of the invention may arise from contact with an infectious agent via any route known in the art, including pneumonias associated with ventilators (e.g., ventilator-associated pneumonia), air-borne infectious agents, infectious agents dispersed in a nebulized fluid such as by sneezing, and the like. In some embodiments, the method prevents respiratory infection by an agent selected from the group consisting of *Bacillus anthracis* and Small Pox Virus.

Yet another aspect of the invention is a method for irrigating at least a portion of the urinary tract in order to prevent a chronic urinary tract infection, comprising the step of delivering an effective amount of a composition comprising PEG to a urethra, wherein the PEG has an average molecular weight of at least 5,000 daltons. In one embodiment, the composition is administered to a portion of the urinary tract that includes at least the bladder.

Another aspect of the invention is a method of preventing a sexually transmitted disease comprising the step of applying polyethylene glycol (PEG) to a condom, wherein the PEG has an average molecular weight of at least 5,000 daltons. A related aspect of the invention is a condom comprising at least a partial coating with PEG having an average molecular weight of at least 5,000 daltons. Yet another related aspect is a kit comprising a condom and polyethylene glycol (PEG) having an average molecular weight of at least 5,000 daltons.

The invention also comprehends a method of preventing a digestive tract disorder comprising administering an effective dose of a composition comprising polyethylene glycol (PEG) to an animal in need thereof, wherein the PEG has an average molecular weight of at least 5,000 daltons. Exemplary digestive tract disorders amenable to the preventive methods of the invention may be selected from the group consisting of neonatal necrotizing enterocolitis, antibiotic-induced diarrhea, pseudomembranous colitis, an inflammatory bowel disease, irritable bowel disease, neutropenic enterocolitis, pancreatitis, dysbiosis syndrome and microscopic colitis.

Another aspect of the invention is a method for monitoring the administration of polyethylene glycol (PEG) to an animal in need thereof, comprising administering an effective amount of a composition comprising labeled PEG, wherein the PEG has an average molecular weight of at least 5,000 daltons, to an animal in need thereof, and detecting the labeled PEG, whereby the quantity and/or location of the labeled PEG (e.g., associated with a microbe) provides information useful in assessing the efficacy of administration. In one embodiment of the monitoring method, the label is a fluorophore (e.g., fluorescein, rhodamine, Cy3, Cy5). In another embodiment of the method, detecting the labeled PEG comprises endoscopic inspection. The monitoring method also contemplates that the labeled PEG is detected in a stool sample (i.e., the labeled PEG associates with a component such as a microbe, whose source is a stool sample). In addition, the monitoring method may further comprise administering a second label specific for a microbe and detecting the second label. "Specific" as used in this context means that the label is detectably associable with at least one microbe.

Another aspect of the invention is a method for monitoring the administration of polyethylene glycol (PEG) to an animal in need thereof, comprising obtaining a sample from an animal receiving polyethylene glycol, wherein the PEG has an average molecular weight of at least 5,000 daltons, contacting the sample with an epithelial cell, and measuring the adherence of a microbe in the sample to the epithelial cell, whereby the quantity and/or location of the PEG provides information useful in assessing the efficacy of administration. The measuring may be accomplished by microscopic examination.

Another monitoring method according to the invention is a method for monitoring the administration of polyethylene glycol (PEG) to an animal in need thereof, comprising obtaining a sample from an animal receiving polyethylene glycol, wherein the PEG has an average molecular weight of at least 5,000 daltons, contacting the epithelial cell layer with the sample, and measuring a trans-epithelial electrical resistance of the epithelial layer, whereby effective administration is indicated by a reduced decrease in trans-epithelial electrical resistance relative to a control value. The control value may be internal (i.e., measuring the TEER prior to PEG administration) or external (i.e., a value developed in other studies that is reliably used for comparison).

Yet another monitoring method of the invention is a method for monitoring the administration of polyethylene glycol (PEG) to an animal in need thereof, comprising obtaining a sample from an animal receiving polyethylene glycol, wherein the PEG has an average molecular weight of at least 5,000 daltons, isolating a microbe from the sample, and measuring the hydrophobicity of the cell surface of the microbe, whereby the hydrophobicity of any microbe in the sample provides information useful in assessing the efficacy of administration. "Isolating," as used in this context, means separated from other components of the sample (e.g., solid matter) sufficiently to permit hydrophobicity measurements, as would be understood in the art.

A related aspect of the invention is a kit for monitoring the administration of polyethylene glycol, comprising a labeled PEG and a protocol describing use of the labeled PEG in monitoring administration thereof. Suitable protocols include any of the methods disclosed herein or known in the art relating to the administration, delivery or application of PEG. In some embodiments of this aspect of the invention, the kit further comprises a free label.

Still another monitoring method of the invention is a method for monitoring the administration of polyethylene glycol (PEG) to an animal in need thereof, comprising obtaining a sample from an animal receiving polyethylene glycol, wherein the PEG has an average molecular weight of at least 5,000 daltons, and detecting PA-I lectin/adhesin activity in the sample, whereby the PA-I lectin/adhesin activity provides information useful in assessing the efficacy of administration. In one embodiment of this method, the PA-I lectin/adhesin is detected by binding to a PA-I lectin/adhesin binding partner, such as any known form of a specific anti-PA-I lectin/adhesin antibody or a carbohydrate to which the lectin/adhesin specifically binds. A related aspect of the invention is a kit for monitoring the administration of polyethylene glycol (PEG) comprising a PA-I lectin/adhesin binding partner and a protocol describing use of the binding partner to detect PA-I lectin/adhesin in the sample. Suitable protocols include any of the methods disclosed herein or known in the art relating to the use of PEG.

Other features and advantages of the present invention will be better understood by reference to the following detailed description, including the drawing and the examples.

PA27853 into the cecum. Mice underwent a 30% bloodless left lobe hepatectomy immediately, followed by direct cecal injection of $1\times10^7$ cfu/ml of PA27853. Each group contained 7 mice. Control mice underwent sham laparotomy followed by injection of equal amounts of PA27853 into the cecum. For mice in the PEG groups, $1\times10^7$ cfu/ml of PA27853 was suspended in either PEG 3.35 (LMW PEG 3,350) or PEG 15-20 (HMW PEG 15,000 to 20,000 daltons) prior to cecal injection. Dose response curves for PEG 15-20 are seen in panel b. a. A statistically significant protective effect of PEG 15-20 was determined by the Fisher Exact Test (P<0.001). b. The minimum protective concentration of PEG 15-20 was determined to be 5% (P<0.05). c. Quantitative bacterial cultures of cecal contents (feces), washed cecal mucosa, liver, and blood 24 hours following 30% surgical hepatectomy and direct cecal injection of $1\times10^7$ cfu/ml of PA27853. One-way ANOVA demonstrated a statistically significant increase in bacterial counts in cecal contents, mucosa, liver, and blood in mice following hepatectomy (P<0.001). A significant decrease (P<0.05) in the liver and blood bacterial counts was observed for PEG 3350, while PEG 15-20 completely prevented PA27853 from disseminating to the liver and blood of mice.

Figure 2:
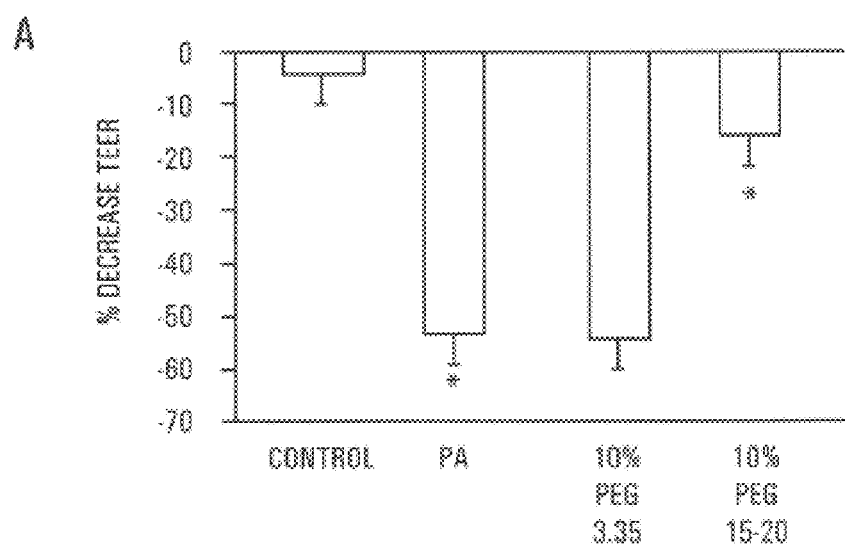
Figure 2:
Figure 2:

FIG. 2 shows the protective effect of PEG 15-20 against PA27853-induced epithelial barrier dysfunction as assessed by transepithelial electrical resistance (TEER). a. Data represent the mean±SEM % maximal fall in TEER from baseline of triplicate cultures (n=7) observed during 8 hours of apical exposure to $1\times10^7$ cfu/ml of PA27853. A statistically significant decrease in TEER was demonstrated (one-way ANOVA (P<0.001)) in Caco-2 cells exposed to PA27853. A statistically significant protective effect on the fall in TEER induced by PA27853 was demonstrated for PEG 15-20 (P<0.001). b. Image of Caco-2 cells in the presence of PEG 3.35 and apical exposure to PA27853. Images taken after 4 hours of co-culture demonstrated loss of monolayer integrity with cells floating 30-40 microns above the cell scaffolds displaying adherence of PA27853 to cell membranes. c. Caco-2 cells apically exposed to PA27853 after 4 hours in the presence of PEG 15-20 showed no evidence of floating cells in any of the planes examined.

Figure 3:
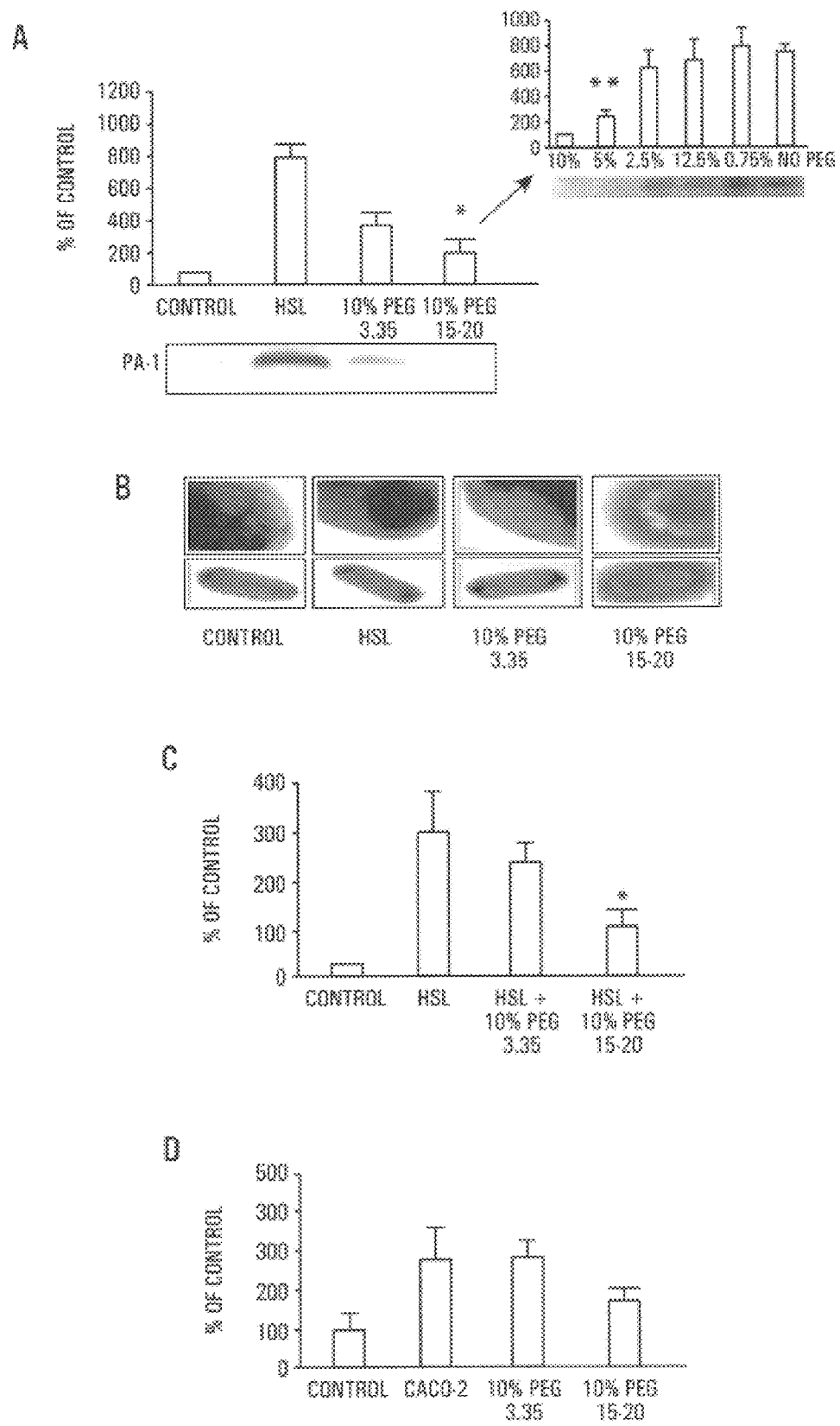

FIG. 3 illustrates the inhibitory effect of PEGs on PA-I expression in PA27853. a. Western blot analysis. Exposure of PA27853 to 1 mM of the quorum-sensing signaling molecule C4-HSL resulted in a statistically significant increase (P<0.001 one-way ANOVA) in PA-I protein expression that was partially inhibited in the presence of 10% PEG 3.35 and much more inhibited with 10% PEG 15-20. a'. The minimum inhibitory concentration of PEG 15-20 on C4-HSL induced PA-I expression was 5% (P<0.01). b. Electron microscopy of individual bacteria cells exposed to C4-HSL in the presence and absence of PEGs, demonstrated that C4-HSL caused a morphological change in the shape and pili expression of P. aeruginosa. The C4-HSL-induced morphological effect was completely eliminated in the presence of PEG 15-20, but not PEG 3.35. A halo-type effect can be seen surrounding PA27853 exposed to PEG 15-20. c. Northern hybridization. Exposure of PA27853 to 0.1 mM of C4-HSL resulted in a statistically significant increase (P<0.001 one-way ANOVA) in PA-I mRNA expression that was greatly inhibited with 10% PEG 15-20. d. The increase in PA-I mRNA induced by 4 hours exposure to Caco-2 cell was inhibited in the presence of PEG 15-20, but not PEG 3.35 (P<0.001 one-way ANOVA).

Figure 4:
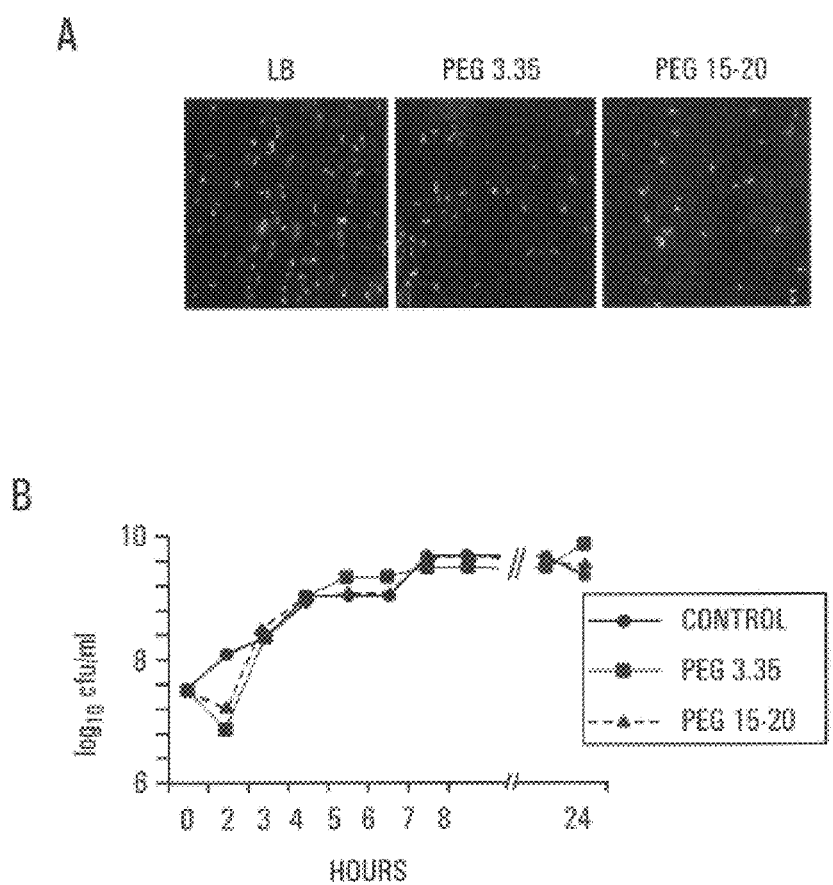

FIG. 4 shows the effect of PEG solutions on bacterial membrane integrity arid growth patterns of PA27853. a. The effect of the two PEG solutions on bacterial membrane integrity was assessed by a staining method consisting of SYTO 9 and propidium iodide. Neither PEG solution had any effect on bacterial membrane permeability. b. PA27853 growth patterns appeared identical in the two PEG solutions relative to the PEG-free TSB medium (control).

Figure 5:
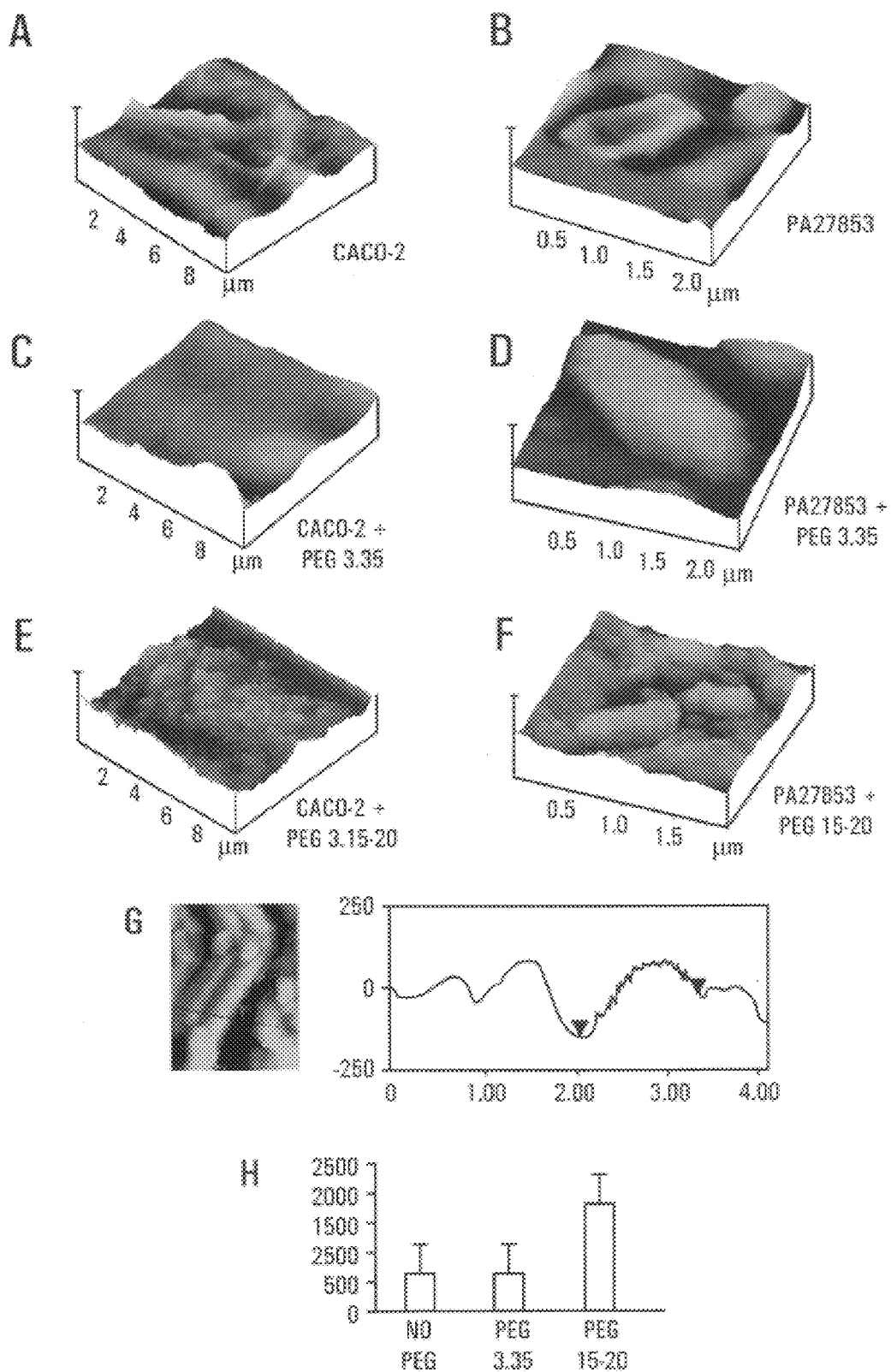

FIG. 5 presents Atomic Force Microscopy (AFM) images of Caco-2 cells and bacterial cells exposed to PEGs. a.-c. AFM images of Caco-2 cells in the presence of medium alone (a), medium with PEG 3.35 (b), and medium with PEG 15-20. PEG 3.35 was seen to form a smooth carpet over the Caco-2 cells (b), whereas PEG 15-20 formed a more topographically defined covering (c). d.-f. AFM images of PA27853 in PEG 3.35 and PEG 15-20. PEG 3.35 formed a smooth envelope around individual bacterial cells (e) whereas PEG 15-20 not only tightly hugged the individual cells (f), but also increased the polymer/bacterial diameter (g,h), thereby distancing individual bacteria from one another.

Figure 6:
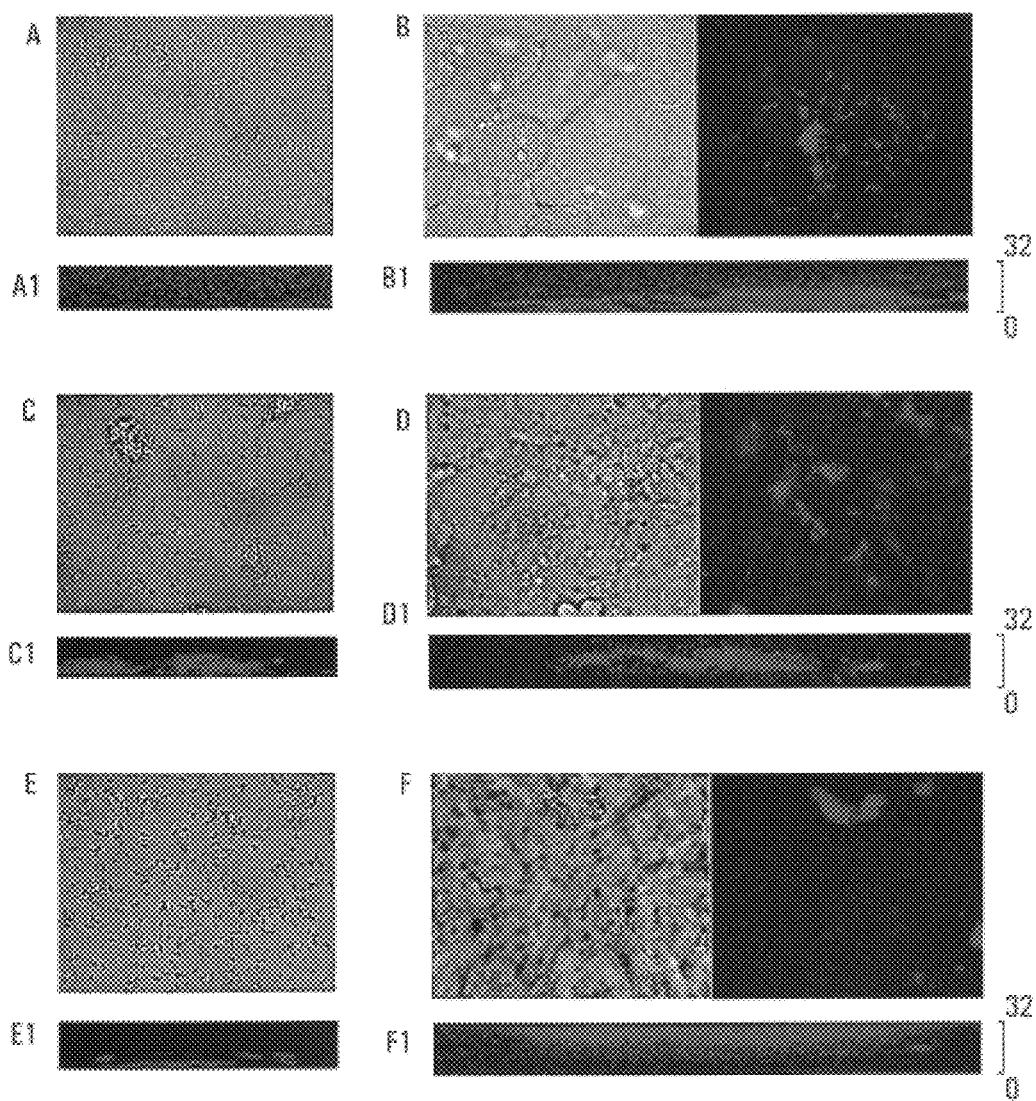

FIG. 6 shows the effect of PEG solution on the dispersion/clumping pattern of PA27853. The dispersion pattern of bacterial cells in dTC3 dishes was observed directly with an Axiovert 100 TV fluorescence inverted microscope using DIC and GFP fluorescence filter, at an objective magnification of 63×. Temperature was adjusted with a Bioptechs thermostat temperature control system. Tungsten lamps (100 V) were used for both DIC and the GFP excitation. The 3D imaging software (Slidebook) from intelligent Imaging Innovations was used to image the bacterial cell dispersion pattern in the Z plane using the GFP filter. Uniformly dispersed planktonic P. aeruginosa cells in the medium without Caco-2 cells were seen on DIC image ($6a_1$) and Z plane reconstruction ($6a_2$). In the presence of Caco-2 cells, bacterial cells developed a clumped appearance ($6b_1$) and were seen adherent to the Caco-2 cells ($6b_2$). 10% PEG 3350 decreased the motility of bacteria and induced immediate formation of mushroom-shaped bacterial microcolonies ($6c_1$) adhering to the bottom of the well ($6c_2$). In the presence of Caco-2 cells, bacterial microcolonies were on the order of 8 microns above the plane of the epithelial cells ($6d_{1,2}$). 10% PEG 15-20 greatly diminished the motility of P. aeruginosa cells. Nevertheless, for the first 0.5-1 hours of incubation in PEG 15-20-containing medium, bacterial cells formed spider-shaped microcolonies that were close to the bottom of the well ($6e_{1,2}$). Within several hours, spider leg-shaped microcolonies occupied the entire space/volume of the medium (not shown). In the presence of Caco-2 cells, P. aeruginosa cells lost the spider-like configuration and were seen elevated high above the plane of the epithelium (30-40 microns) ($6f_{1,2}$).

DETAILED DESCRIPTION OF INVENTION

The invention provides products and methods that collectively present simple and economical approaches to the treatment and/or prevention of a variety of microbe-mediated epithelial disorders, i.e., abnormal conditions and diseases, that afflict many mammals, including humans. By administering high molecular weight polar polymers such as HMW polyethylene glycol to an animal in need, including those at risk, any of a number of health- or life-threatening abnormal conditions, i.e., epithelial disorders and diseases, including gut-derived sepsis, can be treated with minimal cost and minimal training of practitioners. Without wishing to be bound by theory, the benefits provided by the invention are consistent with the principle that microbe-mediated epithelial disorders can be successfully prevented, ameliorated or treated by facilitating an environment conducive to the survival of such microbes. An understanding of the following more detailed description of the invention is facilitated by initially establishing the following meanings for terms used in this disclosure.

An "abnormal condition" is broadly defined to include mammalian diseases, mammalian disorders and any abnormal state of mammalian health that characterized by an epithelial surface at risk of developing a microbial-mediated disorder. The abnormal conditions characterized by an epithelial surface at risk of developing a microbial-mediated disorder include conditions in which the epithelial surface has developed a microbial-mediated disorder. Exemplary conditions include human diseases and human disorders requiring, or resulting from, medical intervention, such as a burn injury, neonatal enterocolitis, severe neutropenia, inflammatory bowel disease, enteropathy (e.g., of the critically ill) and transplant (e.g., organ) rejection.

"Burn injury" means damage to mammalian tissue resulting from exposure of the tissue to heat, for example in the form of an open flame, steam, hot fluid, and a hot surface.

"Severe" neutropenia is given its ordinary and accustomed meaning of a marked decrease in the number of circulating neutrophils.

"Transplant rejection" refers to any development of transplanted material (e.g., an organ) recognized as being associated with ultimate rejection of that material by the host organism.

"Administering" is given its ordinary and accustomed meaning of delivery by any suitable means recognized in the art. Exemplary forms of administering include oral delivery, anal delivery, direct puncture or injection, topical application, and spray (e.g., nebulizing spray), gel or fluid application to an eye, ear, nose, mouth, anus or urethral opening.

An "effective dose" is that amount of a substance that provides a beneficial effect on the organism receiving the dose and may vary depending upon the purpose of administering the dose, the size and condition of the organism receiving the dose, and other variables recognized in the art as relevant to a determination of an effective does. The process of determining an effective dose involves routine optimization procedures that are within the skill in the art.

An "animal" is given its conventional meaning of a non-plant, non-protist living being. A preferred animal is a mammal, such as a human.

In the context of the present disclosure, a "need" is an organismal, organ, tissue, or cellular state that could benefit from administration of an effective dose to an organism characterized by that state. For example, a human at risk of developing gut-derived sepsis, or presenting a symptom thereof, is an organism in need of an effective dose of a product, such as a pharmaceutical composition, according to the present invention.

"Average molecular weight" is given its ordinary and accustomed meaning of the arithmetic mean of the molecular weights of the components (e.g., molecules) of a composition, regardless of the accuracy of the determination of that mean. For example, polyethylene glycol, or PEG, having an average molecular weight of 3.5 kilodaltons may contain PEG molecules of varying molecular weight, provided that the arithmetic mean of those molecular weights is determined to be 3.5 kilodaltons at some level of accuracy, which may reflect an estimate of the arithmetic mean, as would be understood in the art. Analogously, PEG 15-20 means PEG whose molecular weights yield an arithmetic mean between 15 and 20 kilodaltons, with that arithmetic mean subject to the caveats noted above. These PEG molecules include, but are not limited to, simple PEG polymers. For example, a plurality of relatively smaller PEG molecules (e.g., 7,000 to 10,000 daltons) may be joined, optionally with a linker molecule such as a phenol, into a single molecule having a higher average molecular weight (e.g., 15,000 to 20,000 daltons).

"Cell membrane integrity" means the relative absence of functionally significant modifications of a cell membrane as a functional component of a living cell, as would be understood in the art.

"Detectably altered" is given its ordinary and accustomed meaning of a change that is perceivable using detection means suitable under the circumstances, as would be understood in the art.

"Growth pattern" refers collectively to the values of those properties of a cell, or group of cells (e.g., a population of cells), that are recognized in the art as characterizing cell growth, such as the generation or doubling time of the cell, the appearance of topography of a nascent group of cells, and other variables recognized in the art as contributing to an understanding of the growth pattern of a cell or group of cells.

"Inhibiting" is given its ordinary and accustomed meaning of inhibiting with, reducing or preventing. For example, inhibiting morphological change means that morphological change is made more difficult or prevented entirely.

"PA-I, or PA-I lectin/adhesin, expression means the production or generation of an activity characteristic of PA-I lectin/adhesin. Typically, PA-I lectin/adhesin expression involves translation of a PA-I lectin/adhesin-encoding mRNA to yield a PA-I lectin/adhesin polypeptide having at least one activity characteristic of PA-I lectin/adhesin. Optionally, PA-I lectin/adhesin further includes transcription of a PA-I lectin/adhesin-encoding DNA to yield the aforementioned mRNA.

"Epithelium-induced activation" refers to an increase in the activity of a given target (e.g., PA-I lectin/adhesin) through direct or indirect influence of an epithelial cell. In the context of the present invention, for example, epithelium-induced activation of PA-I lectin/adhesin refers to an increase in that polypeptide's activity attributable to the indirect influence of an epithelium manifested through the direct contact of an epithelial cell or cells with an intestinal pathogen.

"Morphological change" is given its ordinary and accustomed meaning of an alteration in form.

"Intestinal pathogen" means a pathogenic microbe capable of causing, in whole or part, gut-derived sepsis in an animal such as a human. Intestinal pathogens known in the art are embraced by this definition, including gram negative bacilli such as the Pseudomonads (e.g., *Pseudomonas aeruginosa*).

"Ameliorating" means reducing the degree or severity of, consistent with its ordinary and accustomed meaning.

"Pathogenic quorum" means aggregation or association of a sufficient number of pathogenic organisms (e.g., *P. aeruginosa*) to initiate or maintain a quorum sensing signal, as would be known in the art.

"Interaction" is given its ordinary and accustomed meaning of interplay, as in the interplay between or among two or more biological products, such as molecules, cells, and the like.

"Transepithelial Electrical Resistance," or TEER, is given the meaning this phrase has acquired in the art, which refers to a measurement of electrical resistance across epithelial tissue, which is non-exclusively useful in assessing the status of tight junctions between epithelial cells in an epithelial tissue.

"Adherence" is given its ordinary and accustomed meaning of physically associating for longer than a transient period of time.

"Topographically asymmetrical" refers to an image, map or other representation of the surface of a three-dimensional object (e.g., a cell) that is not symmetrical.

"Atomic force microscopy," also known as scanning force microscopy, is a technique for acquiring a high-resolution topographical map of a substance by having a cantilevered probe traverse the surface of a sample in a raster scan and using highly sensitive means for detecting probe deflections, as would be understood in the art.

"Pharmaceutical composition" means a formulation of compounds suitable for therapeutic administration, to a living animal, such as a human patient. Preferred pharmaceutical compositions according to the invention comprise a solution balanced in viscosity, electrolyte profile and osmolality, comprising an electrolyte, dextran-coated L-glutamine, dextran-coated inulin, lactulase, D-galactose, N-acetyl D-galactosamine and 5-20% PEG (15,000-20,000).

"Adjuvants," "carriers," or "diluents" are each given the meanings those terms have acquired in the art. An adjuvant is one or more substances that serve to prolong the immunogenicity of a co-administered immunogen. A carrier is one or more substances that facilitate the manipulation, such as by translocation of a substance being carried. A diluent is one or more substances that reduce the concentration of, or dilute, a given substance exposed to the diluent.

"HMW PEG" refers to relatively high molecular weight PEG defines as having an average molecular weight greater than 3.5 kilodaltons. Preferably, HMW PEG has an average molecular weight greater than 5 kilodaltons and, in particular embodiments, HMW PEG has an average molecular weight at least 8 kilodaltons, at least 15 kilodaltons, and between 15 and 20 kilodaltons.

The following examples illustrate embodiments of the invention. Example 1 describes the protection against gut-derived sepsis provided to hepatectomized mice by high molecular weight PEG. Example 2 discloses how HMW PEG prevents pathogen adherence to intestinal epithelial cells. Example 3 reveals how HMW PEG inhibits pathogenic virulence expression generally, and PA-I lectin/adhesin expression specifically. Example 4 shows that PEG does not affect growth, or cell membrane integrity, of pathogens. Example 5 illustrates the unique topographical conformation of HMW PEG-coated pathogens using Atomic force microscopy. Example 6 describes the cell-cell interactions affected by HMW PEG. Example 7 describes preventive methods using the compositions of the invention. Example 8 discloses methods for monitoring administration of HMW PEG, such as in the treatment methods of the invention, and corresponding kits.

EXAMPLE 1

HMW PEG Protects Against Gut-Derived Sepsis Following 30% Hepatectomy

Male Balb/c mice were anesthetized and subjected to hepatectomy using a conventional protocol. A 30% bloodless excision of the liver along the floppy left lobe was performed. Control mice underwent manipulation of the liver without hepatectomy. The experimental and control groups each contained seven mice. In all mice, a volume of 200 µl of $10^7$ cfu/ml of *Pseudomonas aeruginosa* PA27853 was injected into the base of the cecum by direct needle puncture diluted in either saline, PEG 3.350 or PEG 15-20 (PEGs). The relatively low molecular weight PEGs are commercially available; PEG 15-20, having an average molecular weight of 15,000 to 20,000 daltons, is a combination of PEG 7-8 and PEG 8-10 covalently joined to a phenol ring. The PEG 7-8 has an average molecular weight of 7,000 to 8,000 daltons and the PEG 8-10 has an average molecular weight of 8,000 to 10,000 daltons. One of skill in the art will realize that HMW PEGs include compounds having any of a variety of PEG subunits with each subunit having any of a variety of average molecular weights joined, preferably covalently, to each other or to one or more linker molecules, which are relatively small molecules having functional groups suitable for joinder of PEG molecules. Suitable linkers substantially preserve the biological activity of HMW PEG (preservation of sufficient biological activity to realize a beneficial prophylactic or therapeutic effect as disclosed herein).

In order to provide a constant source of PEG for the 48-hour duration of the experiment, the needle was directed into the small bowel (ileum) and 1 ml of saline, PEG 3.35 or PEG 15-20 was injected retrograde into the proximal bowel. The puncture site was tied off with a silk suture and the cecum swabbed with alcohol. Mice were returned to their cages and were given $H_2O$ only for the next 48 hours.

Figure 1:
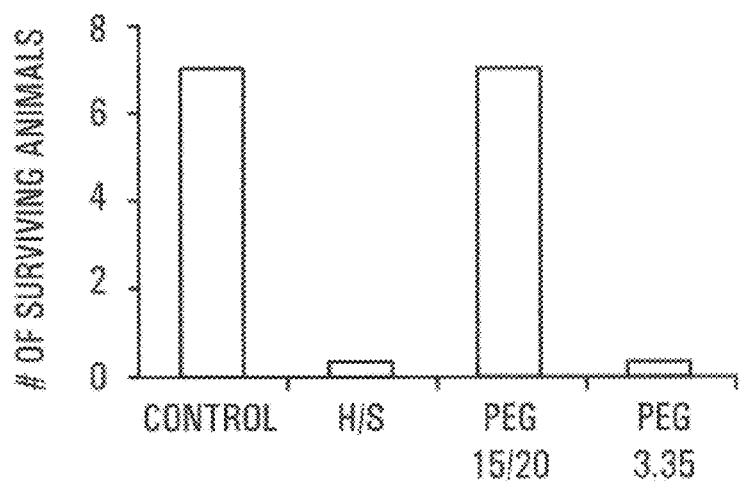
FIG. 1 provides mortality rates in mice at 48 hours subjected to either sham laparotomy or 30% surgical hepatectomy followed by direct injection of *P. aeruginosa*
Figure 1:
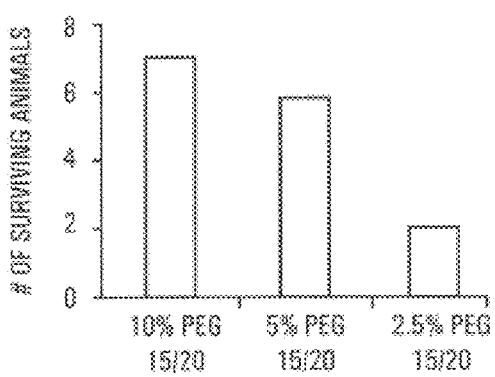
Figure 1:
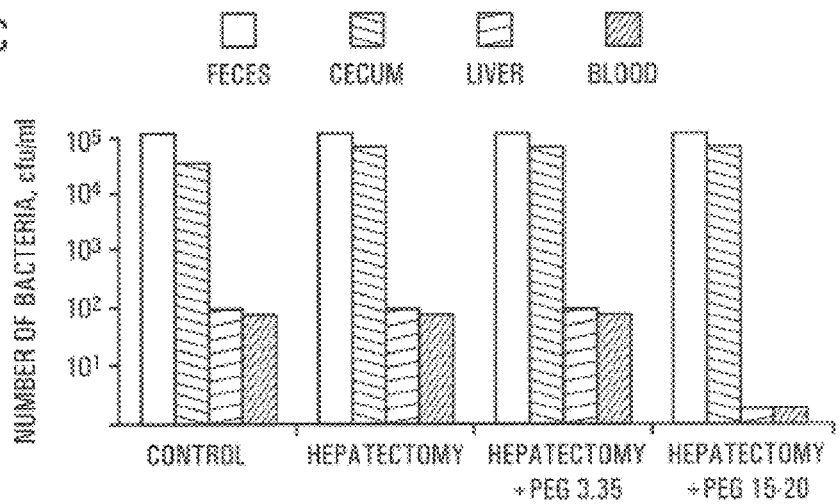

Dose response curves for PEG 15-20 are seen in panel b of FIG. 1. a. A statistically significant protective effect of PEG 15-20 was determined by the Fisher Exact Test ($P<0.001$). b. The minimum protective concentration of PEG 15-20 was determined to be 5% ($P<0.05$). c. Quantitative bacterial cultures of cecal contents (feces), washed cecal mucosa, liver, and blood 24 hours following 30% surgical hepatectomy and direct cecal injection of $1 \times 10^7$ cfu/ml of PA27853. One-way ANOVA demonstrated a statistically significant increase in bacterial counts in cecal contents, mucosa, liver, and blood in mice following hepatectomy ($P<0.001$). A significant decrease ($P<0.05$) in the liver and blood bacterial counts was observed for PEG 3350, while PEG 15-20 completely prevented PA27853 from disseminating to the liver and blood of mice.

*Pseudomonas aeruginosa* strain ATCC 27853 (PA27853) is a non-mucoid clinical isolate from a blood culture. Direct cecal injection of strain PA27853 in mice previously subjected to a 30% bloodless surgical hepatectomy resulted in a state of clinical sepsis and no survivors at 48 hours. Mice subjected to sham laparotomy without hepatectomy (controls), who are similarly injected with *P. aeruginosa*, survive completely without any clinical signs of sepsis (FIG. 1a). To determine the ability of PEG solutions to prevent or lower mortality in this model, 200 µl of PA27853 at a concentration of $1 \times 10^7$ cfu/ml, was suspended in one of two 10% (w/v) solutions of polyethylene glycol (PEG-3.35 versus PEG-15-20). PEG-3.35 was chosen as it represents the molecular weight of PEGs that have been available for clinical use for the last 25 years (Golytely®). In comparison, PEG solutions according to the invention that were used had molecular weights varying between 15-20 kDa. Suspended strains were introduced into the cecum by direct puncture. PEG 3.35 had no effect on mortality in mice following hepatectomy, whereas PEG 15-20 was completely protective. In fact, PEG 15-20 had a statistically significant protective effect, as determined by the Fisher Exact Test ($P<0.001$). Dose-response experiments demonstrated a 5% solution to be the minimal concentration of PEG 15-20 that was completely protective ($P<0.05$; see FIG. 1b), although one of skill in the art will recognize that HMW PEG solutions of less than 5% would be expected to provide some protection and, thus, fall within the scope of the present invention. With respect to bacterial counts in the experimental and control mice, a one-way analysis of variance (ANOVA) demonstrated a statistically significant increase in bacterial counts in the cecal contents, mucosa, liver, and blood in mice following hepatectomy (P<0.001). A significant decrease (P<0.05) in the liver and blood bacterial counts was observed for PEG 3350, while PEG 15-20 completely prevented PA27853 from disseminating to the liver and blood of mice. PEG 15-20 completely inhibited the dissemination of intestinal PA27853 to the liver and bloodstream (FIG. 1c). The data indicate that the action of PEG solutions involves mechanisms that are non-microbiocidal. Given at PEG concentrations non-toxic to mammalian cells (i.e. ≤about 10%), no effect on bacterial growth patterns can be demonstrated.

The example demonstrates that HMW PEG reduces the mortality rate attributable to gut-derived sepsis in mice subjected to surgical intervention in the form of a partial hepatectomy. This mouse model indicates that HMW PEG therapy is useful in reducing the mortality rate of an animal species (i.e., reducing the likelihood of mortality in any given organism), such as a mammal like man, subjected to a physiological stress such as invasive surgery (e.g., partial hepatectomy). It is expected that HMW PEG therapy will be effective in methods of preventing death or serious illness associated with sepsis when implemented following the physiological stress (e.g., during post-operative care). Further, HMW PEG therapy may be used prior to physiological stressing (e.g., pre-operative care), under circumstances where introduction of the stress is predictable, to lower the risk of serious illness or death. HMW PEG therapy is also useful in ameliorating a symptom associated with a disease or abnormal condition associated with gut-derived sepsis.

EXAMPLE 2

HMW PEG Prevents Pathogen Adherence to Intestinal Epithelia

Tight junctions are dynamic elements of the epithelial cell cytoskeleton that play a key role in the barrier function of the mammalian intestinal tract. *P. aeruginosa* results in a profound alteration in tight junctional permeability as measured by the transepithelial electrical resistance (TEER) of both Caco-2 cells and T-84 cells. Caco-2 cells are well-characterized human colon epithelial cells that maintain a stable TEER in culture, and this cell line provides a recognized in vitro model of the in vivo behavior of intestinal pathogens. To determine the protective effect of PEG on *P. aeruginosa* PA27853-induced decreases in TEER of cultured Caco-2 monolayers, $1 \times 10^7$ cfu/ml of PA27853 was apically inoculated onto two Caco-2 cell monolayers in the presence of 10% PEG 3.35 or 10% PEG 15-20. TEER was serially measured for 8 hours and the maximal fall in TEER recorded.

Only PEG 15-20 protected significantly against the *P. aeruginosa*-induced decrease in TEER (FIG. 2a). The data presented in FIG. 2 represent the mean±SEM % maximal fall in TEER from baseline of triplicate cultures (n=7) observed during 8 hours of apical exposure to $1 \times 10^7$ cfu/ml of PA27853. A statistically significant decrease in TEER, as demonstrated in Caco-2 cells exposed to PA27853, was revealed by one-way ANOVA (P<0.001). A statistically significant protective effect on the fall in TEER induced by PA27853 was demonstrated for PEG 15-20 (P<0.001). FIG. 2b shows Caco-2 cells in the presence of PEG 3.35 and with apical exposure to PA27853. After 4 hours of co-culture in the presence of PEG 3.35, disruption of the Caco-2 cell monolayers displaying focally adherent bacteria was observed, with cells floating 30-40 microns above the monolayer scaffolds (FIG. 2b). In contrast, FIG. 2c, showing images of Caco-2 cells apically exposed for 4 hours to PA27853 in the presence of PEG 15-20, shows no evidence of floating cells in any of the planes examined. The protective effect of PEG 15-20 on Caco-2 cell integrity was associated with less bacterial adherence, reflected by a 15-fold higher recovery of bacteria in the cell supernatants following a 4-hour exposure to $1 \times 10^6$ cfu/ml of PA27853.

The resistance of PEG-cultured human intestinal epithelial cells to the barrier-disrupting effects of *P. aeruginosa*, as judged by the maintenance of TEER, offers a practical approach to stabilizing tight junctional barrier function in the face of a challenge from invading pathogens. Further evidence of the therapeutic value of PEG 15-20 is that epithelial transport function ($Na^+/H^+$ exchange, glucose transport) is unaffected by this compound.

Thus, HMW PEG is relatively inert to, and has a stabilizing effect on, the intestinal epithelial barrier. The invention comprehends methods of treating intestinal barrier abnormalities associated with intestinal pathogens such as *P. aeruginosa* by administering HMW PEG to an animal such as a mammal and, preferably, a human. An intestinal barrier abnormality may be revealed by any diagnostic technique, or other means, known in the art. It is not necessary to identify an intestinal barrier abnormality prior to HMW PEG treatment, however. The low cost and high degree of safety associated with HMW PEG treatment make this approach suitable for both prophylactic applications, preferably directed towards at-risk organisms, as well as treatment methods applied to animals exhibiting at least one symptom characteristic of an intestinal barrier abnormality. The HMW PEG treatment methods would ameliorate a symptom associated with an intestinal barrier abnormality; preferably, the methods would reduce or eliminate the effects of gut-derived sepsis from a treated organism.

EXAMPLE 3

HMW PEG Inhibits Virulence Expression in Pathogens

The expression of the PA-I lectin/adhesin in *P. aeruginosa* PA27853 was increased in the cecum of mice following hepatectomy and played a key role in the lethal effect of *P. aeruginosa* in the mouse intestine. PA-I functions as a significant virulence determinant in the mouse intestine by facilitating the adherence of PA27853 to the epithelium as well as by creating a significant barrier defect to the cytotoxins, exotoxin A and elastase. PA-I expression in *P. aeruginosa* is regulated by the transcriptional regulator RhIR and its cognate activator C4-HSL. Expression of PA-I in PA27853 was not only increased by exposure to C4-HSL, but also by contact with Caco-2 cells, Caco-2 cell membrane preparations, and supernatants from Caco-2 cell cultures.

Northern hybridization was used to analyze the expression of PA-I at the transcriptional level. Total RNA of *P. aeruginosa* was isolated by the modified three-detergent method. Probes were generated by PCR using PA-I primers: F(ACCCTGGACATTATTGGGTG) (SEQ ID NO: 1), R(CGATGTCATTACCATCG-TCG) (SEQ ID NO: 2) and 16S primers: F(GGACGGGTGAGTAATGCCTA) (SEQ ID NO: 3), R(CGTAAGGGCCATGATGACTT) (SEQ ID NO: 4), and cloned into the pCR2.1 vector (Invitrogen, Inc.). The inserts were sequences that matched the sequence of either PA-I or 16S. Specific cDNA probes for PA-I and 16S were radiolabeled with $\alpha^{32}$P-dCTP. The specific radioactivity was measured by a Storm 860 phosphorimager (Molecular Dynamics, CA), and relative percent changes compared to control were calculated based on the intensity ratio of PA-I and 16S. Western blot was used for PA-I protein analysis, using rabbit affinity-purified polyclonal anti-PA-I antibodies. One ml of P. aeruginosa cells was washed with PBS and heated at 100° C. in lysis buffer (4% SDS, 50 mM Tris-HCl, pH 6.8); immunoblot analysis was performed by electrotransfer of proteins after Tricine SDS-PAGE. The PA-I lectin was detected by the ECL reagent (Amersham, N.J.).

Exposure of P. aeruginosa PA27853 to 1 mM of the quorum-sensing signaling molecule C4-HSL resulted in a statistically significant increase ($P<0.001$, one-way ANOVA) in PA-I protein expression that was partially inhibited in the presence of 10% PEG 3.35 and inhibited to a much greater extent by 10% PEG 15-20 (FIG. 3). The minimum completely inhibitory concentration of PEG 15-20 on C4-HSL-induced PA-I expression was 5% ($P<0.01$, one-way ANOVA). Electron microscopic examination of individual bacterial cells exposed to C4-HSL in the presence and absence of PEG, demonstrated that C4-HSL caused a morphological change in the shape and pili expression of P. aeruginosa (FIG. 3b). The C4-HSL-induced morphological effect was completely eliminated in the presence of PEG 15-20, but not completely eliminated in the presence of PEG 3.35. A halo-type effect was seen surrounding PA27853 exposed to PEG 15-20 (FIG. 3b). Exposure of PA27853 to 0.1 mM of C4-HSL resulted in a statistically significant increase ($P<0.001$, one-way ANOVA) in PA-I mRNA expression assessed using Northern blots. The PA-I expression was greatly inhibited by 10% PEG 15-20. FIG. 3d shows that the increase in PA-I mRNA induced by a 4-hour exposure to Caco-2 cells was inhibited by PEG 15-20, but not by PEG 3.35 ($P<0.001$ one-way ANOVA).

The data presented herein show that a significant attenuation (3-4-fold decrease) of PA-I expression (protein and mRNA) in PA27853, induced by 100 µM-1 mM of C4-HSL, was observed when bacteria were pre-treated with 10% PEG 15-20. This effect was not observed with PEG 3.35 (FIG. 3a). Attenuation of C4-HSL-induced PA-I expression was also observed for 10% PEG 3.35, although the degree of attenuation was significantly less than that for 10% PEG 15-20. The minimum concentration of PEG 15-20 that inhibited C4-HSL induced expression of PA-I protein was 5% (FIG. 3b). Electron microscopy of individual bacterial cells exposed to C4-HSL demonstrated that C4-HSL caused a morphological change in the shape and pili expression of PA27853 (FIG. 3b). The C4-HSL-induced morphological effect was completely eliminated in the presence of PEG 15-20, but not PEG 3.35 (FIG. 3b). PA-I expression (mRNA), induced by 4 hours exposure to Caco-2 cells, was inhibited in the presence of PEG 15-20 but not PEG 3.35 (FIG. 3b). The protective effect of Caco-2 cell-induced PA-I expression with PEG 15-20 persisted in experiments of overnight exposure.

HMW PEG also affects the virulence expression of P. aeruginosa in response to known stimuli. The attenuation of C4-HSL-induced PA-I expression in PA27853 may be a major protective effect of PEG 15-20, given that quorum-sensing signaling is a well-established mechanism of virulence expression for this pathogen. The PEG 15-20-induced interference with Caco-2 cell-induced expression of PA-I is expected to be an important aspect of the protective effect of PEG 15-20. PEG 15-20 was found to have a protective effect on host animals through the attenuation of P. aeruginosa (PA27853) PA-I expression in response to filtered cecal contents (feces) from mice following 30% hepatectomy. The ability of PEG 15-20 to shield P. aeruginosa from host factors that increase its virulence expression is expected to be yet another mechanism by which organisms are protected from gut-derived sepsis.

Accordingly, the invention includes materials in the form of kits and corresponding methods of administering an HMW PEG to an animal to prevent or treat a condition characterized by the expression of a virulence factor or determinant by an intestinal pathogen such as one of the Pseudomonads. A virulence determinant may contribute to virulence directly, or indirectly. An example of an indirect contribution is the effect of the PA/I lectin/adhesin of P. aeruginosa on intestinal pathogen adhesion to intestinal epithelia and/or the generation of a barrier defect to the cytotoxins, exotoxin A and elastase.

EXAMPLE 4

PEG does not Affect Cell Growth, or Cell Membrane Integrity, of Pathogens

The effect of the two PEG solutions (PEG 3.35 and PEG 15-20) on bacterial membrane integrity was assessed by a staining method consisting of SYTO 9 and propidium iodide. Neither PEG solution had any effect on bacterial membrane permeability (FIG. 4a). Membrane integrity was determined using a live/dead bacterial viability kit L-3152 (Molecular Probes). Bacteria were quantified and counts expressed as cfu/ml by plating 10-fold dilutions of samples taken at different incubation times. Growth curves for P. aeruginosa grown overnight in TSB media containing either of the two PEG solutions demonstrated no inhibitory effect by either PEG solution on bacterial quantity (FIG. 4b). In fact, the growth pattern in each of the PEG-containing media was indistinguishable from the growth pattern in PEG-free TSB medium. The activity of a housekeeping enzyme involved in energy metabolism, lactate dehydrogenase (LDH), was measured at various time points during the exponential and stationary phases of growth. LDH activity was measured in a coupled diaphorase enzymatic assay using a substrate mix from CytoTox 96 (Promega). Protein concentration was determined using the BCA Protein Assay (Pierce). No change in LDH activity in cell-free supernatants of P. aeruginosa grown in the presence of PEGs was observed. The results of this experiment indicate that HMW PEG has a negligible effect on bacterial growth patterns.

The methods of the invention, and corresponding products (e.g., kits), provide the benefit of preventing or treating diseases or abnormal conditions associated with gut-derived sepsis without significantly influencing the composition of the intestinal flora. Similarly, the methods and products of the invention may be used to ameliorate a symptom associated with such diseases or abnormal conditions without significant change to the microbial composition of the intestine. One of skill in the art recognizes that methods (and kits) that do not significantly disturb the composition of the intestinal flora are desirable insofar as such methods would not be expected to lead to secondary health complications arising from such a disturbance.

EXAMPLE 5

Atomic Force Microscopy of PEG-Coated Pathogen

One percent aliquots of a culture of PA27853 grown overnight were subcultured in tryptic soy broth (TSB), with or without 10% HMW PEG, for 4 hours at 37° C. One drop of each subculture was withdrawn and the *P. aeruginosa* PA27853 cells were extensively washed with PBS, dried on top of mica in blowing air for 10 minutes, and imaged immediately. Imaging of the dried bacteria with tapping-mode AFM was performed in air with a Multimode Nanoscope IIIA Scanning Probe Microscope (MMAFM, Digital Instruments). Subconfluent Caco-2 cells were treated with 10% HMW PEG for 4 hours and washed with PBS extensively. AFM imaging of the cells was performed in PBS without using an O-ring. For electron microscopy, PA27853 was inoculated in TSB with or without 1 mM C4-HSL and 10% HMW PEG and incubated overnight. One drop of 1% *P. aeruginosa* was stained with uranyl acetate and washed with 0.5M NaCl before examination under the electron microscope.

Atomic force microscopy of Caco-2 cells demonstrated a classical non-uniform surface with brush border microvili, while Caco-2 cells exposed to PEG 3.35 demonstrated a smooth planar appearance on the surface of the epithelial cells (FIGS. 5a, c). PEG 15-20 appears to carpet the Caco-2 cells by filling the asymmetries along a topographically defined plane (FIG. 5e), yielding a more complex topographically defined covering. In somewhat similar fashion, PA27853 cells exposed to PEG 3.35 demonstrate a pattern of smooth coating of the polymer to bacterial cells in a diffuse flat pattern (FIG. 6d), whereas PEG 15-20 appears to surround and hug the bacteria circumferentially in a more topographically asymmetric fashion. Cross-sectional analysis of the atomic force measurement of the bacterial diameter in PEG 15-20 demonstrates a significant increase in the bacteria/PEG envelope within the PEG solution (FIG. 5e, f). In other words, PEG 3.35 forms a smooth envelope around individual bacterial cells (FIG. 5e), whereas PEG 15-20 tightly hugs individual cells (FIG. 5f) and increases the polymer/bacterial diameter (FIGS. 5g, 5h), thereby distancing individual bacterial cells from each other.

Without wishing to be bound by theory, HMW PEG may exert its beneficial effect by the mere physical distancing of *P. aeruginosa* away from the intestinal epithelium. Alternatively, HMW PEG may provide benefits by preventing formation of a pathogenic quorum-sensing activation signal arising from cell-cell interaction of the pathogenic cells. Again without wishing to be bound by theory, it is possible that the coating of biological surfaces with HMW PEG results in loss of conformational freedom of the coating PEG chains and the repelling of approaching proteins. Polar-polar interactions between HMW PEG and Caco-2 cells could affect the elasticity of the PEG chains, constraining certain HMW PEG side chains to a molecular construct which repels protein. Data presented herein support the conclusion that HMW PEG-coated Caco-2 cells are more repellant to *P. aeruginosa* than uncoated Caco-2 cells, perhaps owing to a loss of "conformational entropy" as a result of some dynamic interaction of HMW PEG with Caco-2 cells.

The results of this experiment establish that HMW PEG treatment has an effect on treated cells, notably affecting the surface topology of such cells. Moreover, the effect of HMW PEG exposure on such cells is different from the effect that PEG 3.35 has on such cells. Although not wishing to be bound by theory, the results disclosed herein do provide a physical correlate for the markedly different effect on cells exhibited by HMW PEG relative to lower molecular weight PEGs, such as PEG 3.35.

EXAMPLE 6

HMW PEG Affects Cell-Cell Interactions

To directly observe the effect of PEG solutions on the spatial orientation of *P. aeruginosa*, experiments were performed with live strains of *P. aeruginosa* PA27853/EGFP harboring the egfp gene encoding the green fluorescent protein. Experiments were performed in the presence and absence of Caco-2 cells. In order to image the effect of PEGs on both the bacteria and their interaction with the cultured epithelia, differential interference contrast (DIC) microscopy and GFP imaging were used.

The EGFP gene encoding green fluorescent protein was amplified using the pBI-EGFP plasmid (Clontech) as a template. XbaI and PstI restriction sites were introduced using primers TCTAGAACTAGTGGATCCCCGCGGATG (SEQ ID NO: 5) and GCAGACTAGGTCGACAAGCTT-GATATC (SEQ ID NO: 6). The PCR product was cloned directly into the pCR 2.1 vector using a TA-cloning kit (Invitrogen), followed by transformation of the pCR2.1/EGFP construct into *E. coli* DH5a. The EGFP gene was excised from this construct by digestion with XbaI and PstI and the fragment containing the excised gene was cloned into the *E. coli-P. aeruginosa* shuttle vector pUCP24, which had been digested with the same restriction enzymes. The resulting construct (i.e., pUCP24/EGFP), containing the EGFP gene in the shuttle vector, was electroporated at 25 μF and 2500 V into PA27583 electro-competent cells. PA27853/EGFP-containing cells were selected on LB-agar plates containing 100 μg/ml gentamicin (Gm).

Cells harboring PA27853/EGFP were grown overnight in LB containing 100 μg/ml Gm, and 1% of the culture was used to inoculate fresh LB containing 50 μg/ml Gm. After 3 hours of growth, Isopropyl-β-D-thiogalactopyranoside (IPTG) was added to a final concentration of 0.5 mM, and cultures were incubated for 2 additional hours. 100 μl of the bacterial culture was mixed with 1 ml of HDMEM media (Gibco BRL) buffered with HEPES and containing 10% fetal bovine serum (HDMEM HF) and 10% HMW PEG. One ml of bacterial suspension was poured into a 0.15 mm-thick dTC3 dish (Bioptech). Four-day-old Caco-2 cells (p10-p30) grown in 0.15 mm-thick dTC3 dishes (Bioptech) in HDMEM HF were washed once in HDMEM HF with or without HMW PEG. One ml of bacterial suspension prepared as above was added to a dTC3 dish containing Caco-2 cells. The dispersion pattern of bacterial cells in dTC3 dishes was observed directly with an Axiovert 100 TV fluorescence inverted microscope using DIC and GFP fluorescence filters, at an objective magnification of 63×. The temperature was adjusted with a Bioptechs thermostat temperature control system. Tungsten lamps (100 V) were used for both DIC and the GFP excitation. The 3D imaging software (Slidebook) from Intelligent Imaging Innovations was used to image the bacterial cell dispersion pattern in the Z plane using the GFP filter. Uniformly dispersed planktonic *P. aeruginosa* cells in the medium without Caco-2 cells were seen on a DIC image (FIG. $6a_1$) and Z plane reconstruction (FIG. $6a_2$). In the presence of Caco-2 cells, bacterial cells developed a clumped appearance (FIG. $6b_1$) and were seen adhering to the Caco-2 cells (FIG. $6b_2$). A solution of 10% PEG 3350 decreased the bacterial motility and induced immediate formation of mushroom-shaped bacterial microcolonies (FIG. $6c_1$) adhering to the bottom of the well (FIG. $6c_2$). In the presence of Caco-2 cells, bacterial microcolonies were approximately 8 microns above the plane of the epithelial cells (FIG. $6d_{1,2}$). A solution of 10% PEG 15-20 greatly diminished the motility of *P. aeruginosa* cells. Nevertheless, for the first 0.5-1 hour of incubation in PEG 15-20-containing medium, bacterial cells formed spider leg-shaped microcolonies that were close to the bottom of the well (FIG. $6e_{1,2}$). Within several hours, spider leg-shaped microcolonies occupied the entire space/volume of the medium. In the presence of Caco-2 cells, *P. aeruginosa* cells lost the spider leg-like configuration and were seen elevated high above the plane of the epithelium (30-40 microns) (FIG. $6f_{1,2}$).

To determine the spatial orientation of the bacterial-epithelial cell interactions in three dimensions, Z plane re-constructions were performed. Images demonstrated that the two PEG solutions had different effects on the clumping behavior of *P. aeruginosa* and differentially affected the spatial orientation of the bacteria depending on the presence or absence of Caco-2 cells. In experiments with medium only, *P. aeruginosa* were seen to display a uniformly dispersed pattern (FIG. 6a). Bacterial cells examined in the presence of Caco-2 cells, however, developed a clumped appearance and were seen adjacent to the plane of the epithelial cells at the bottom of the wells (FIG. 6b). Bacterial cells examined in the presence of PEG 3.35 alone formed large clumped aggregates and remained in the bottom of the culture well (FIG. 6c), whereas bacterial cells examined with Caco-2 cells in medium containing PEG 3.35, remained suspended above the plane of the epithelial cells (about 8 microns), maintaining their clumped appearance (FIG. 6d). Bacterial cells examined in the presence of PEG 15-20 alone displayed a uniform pattern of microclumping (FIG. 6e), whereas bacterial cells examined in the presence of Caco-2 in medium containing PEG 15-20 were suspended higher above the plane of the epithelium (~32 microns) in clumped formation (FIG. 6f). In timed experiments, bacterial motility was observed to be decreased by PEG 3.35 and, to an even greater degree, with PEG 15-20.

In a manner analogous to the experiment disclosed in Example 5, this Example provides a physical correlate for the observed effect of HMW PEG on cell-cell interaction, consistent with its beneficial prophylactic and therapeutic activities as disclosed herein. It is expected that use of HMW PEG will reduce or eliminate deleterious cell-cell interactions in the intestine (e.g., between intestinal epithelial cells and intestinal pathogens such as the Pseudomonads), reducing the risk of diseases and/or abnormal conditions associated with gut-derived sepsis.

EXAMPLE 7

Methods of Preventing Disease/Abnormal Conditions

The invention also provides methods of preventing a variety of diseases and/or abnormal conditions in humans and other animals, particularly other mammals. In these methods, an effective amount of HMW PEG is administered to a human patient or an animal subject in need thereof. The PEG may be administered using a schedule of administration that is determined using routine optimization procedures known in the art. Preferably, the PEG has an average molecular weight of 5,000-20,000 daltons, and more preferably between 10,000-20,000 daltons. It is contemplated that at least 5% HMW PEG is administered. The HMW PEG may be administered in any suitable form, e.g., as a solution, as a gel or cream, as a solution suitable for nebulizing (e.g., for inhalational use), in a pharmaceutical composition comprising the HMW PEG, and in a sterile, isotonic solution suitable for injection into an animal. administration may be accomplished using any conventional route; it is particularly contemplated that the HMW PEG is administered orally or topically. In some embodiments, the HMW PEG composition being administered further comprises a compound selected from the group consisting of dextran-coated L-glutamine, dextran-coated inulin, dextran-coated butyric acid, a fructo-oligosaccharide, N-acetyl-D-galactosamine, dextran-coated mannose, galactose and lactulose. In another embodiment, the administered HMW PEG composition further comprises dextran-coated L-glutamine, dextran-coated inulin, dextran-coated butyric acid, one or more fructo-oligosaccharides, N-acetyl-D-galactosamine, dextran-coated mannose, galactose and lactulose.

The invention provides methods of preventing a variety of diseases and abnormal conditions, such as swimmer's ear, acute or chronic otitis media, ventilator-associated pneumonia, gut-derived sepsis, necrotizing enterocolitis, antibiotic-induced diarrhea, pseudomembranous colitis, inflammatory bowel diseases, irritable bowel disease, neutropenic enterocolitis, pancreatitis, chronic fatigue syndrome, dysbiosis syndrome, microscopic colitis, chronic urinary tract infection, sexually transmitted disease, and infection (e.g., exposure to an environment contaminated by a bioterror agent such as *Bacillus anthracis*, Small Pox Virus, enteropathogenic *E. coli* (EPEC), enterohemorrhagic *E. coli* (EHEC), enteroaggregative *E. coli*, (EAEC), *Clostridium difficile*, rotavirus, *Pseudomonas aeruginosa, Serratia marcescens, Klebsiella oxytocia, Enterobacteria cloacae, Candida albicans, Candida globrata*, and the like). In a preferred embodiment of the method of preventing chronic urinary tract infection, or treating such an infection, the HMW PEG is delivered in the form of a bladder irrigant. For sexually transmitted disease prevention, a composition of the invention is preferably used to lubricate a condom. In a preferred embodiment of a method of preventing infection by a bioterror agent, the composition according to the invention is provided in the form of a gel or cream, suitable for topical application. It is expected that such topical application will be useful in preventing a variety of diseases/abnormal conditions associated with any of the bioterror agents or associated with a variety of chemical or physico-chemical agents that pose a threat to man or animal in terms of survival, health or comfort. Such chemical or physico-chemical agents include those agents capable of burning or otherwise injuring skin and which are rendered inactive or are poorly soluble in the compositions of the invention.

In one embodiment of the preventive methods, male Balb/c mice are anesthetized and an aqueous 5% solution of PEG 15-20 is injected into the base of the cecum by direct needle puncture. In order to provide a constant source of PEG for the 48-hour duration of the experiment, the needle is directed into the small bowel (ileum) and 1 ml of the PEG 15-20 is injected retrograde into the proximal bowel. The puncture site is tied off with a silk suture and the cecum swabbed with alcohol. Mice are returned to their cages and are given $H_2O$ only. Forty-eight hours later, the mice are subjected to a conventional hepatectomy procedure involving a 30% bloodless excision of the liver along the floppy left lobe. Control mice will experience manipulation of the liver without hepatectomy. The preventive treatment involving administration of HMW PEG is expected to reduce or eliminate the incidence of surgery-associated gut-derived sepsis in mice.

These methods are applicable beyond the preventive care of such pets as mice, guinea pigs, dogs and cats to such agriculturally significant animals as cattle, horses, goats, sheep, pigs, chickens, turkeys, ducks, geese, and any other domesticated animal. Moreover, these preventive methods are expected to be applicable to humans, improving the health, and life expectancy, of many patients or candidates at risk of developing a disease and/or an abnormal condition, such as swimmer's ear, acute or chronic otitis media, ventilator-associated pneumonia, gut-derived sepsis, necrotizing enterocolitis, antibiotic-induced diarrhea, pseudomembranous colitis, an inflammatory bowel disease, irritable bowel disease, neutropenic enterocolitis, pancreatitis, chronic fatigue syndrome, dysbiosis syndrome, microscopic colitis, chronic urinary tract infections, sexually transmitted diseases, and infectious agents (e.g., bioterror compositions) that include, but are not limited to, anthrax and small pox. As noted above, the preventive methods comprise administration of a composition comprising at least 5% HMW PEG (5-20 kDa), by any known or conventional administration route, to man or another animal. Preferably, the preventive methods are practiced on those individuals at risk of developing one or more of the aforementioned diseases and/or abnormal conditions, but it is contemplated that the compositions and methods of the invention will be useful in either a prophylactic or therapeutic role to broadly treat or prevent such diseases or abnormal conditions in entire populations or sub-populations of man or other animals.

EXAMPLE 8

Methods of Monitoring Administration of HMW PEG

The invention also contemplates methods for monitoring administration of HMW PEG, e.g., in a method of treatment. In such monitoring methods, labeled HMW PEG is administered, alone or in combination with unlabeled HMW PEG, and the label is detected during treatment on a continuous or intermittent schedule, including simple endpoint determinations. The term "labeled" HMW PEG means that a label, or detectable compound, is directly or indirectly attached to HMW PEG, or the HMW PEG is attached to a reporter compound that is capable of associating a label with HMW PEG (of course, labels not attached to HMW PEG or designed to be associated therewith are also contemplated by the invention, as noted below). The HMW PEG is labeled using any detectable label known in the art, and the PEG is labeled to a level sufficient to detect it. Those of skill in the art will recognize that the level will vary depending on the label and the method of detection. One of skill in the art will be able to optimize the degree of labeling using routine optimization procedures. The label is chemically bound to the HMW PEG by a non-covalent or a covalent bond that is stable in use and, preferably, in storage. Label covalently bound to HMW PEG is preferred. The density of label attachment is adjusted to substantially preserve the biological activity of HMW PEG (preservation of sufficient biological activity to realize a beneficial prophylactic or therapeutic effect as disclosed herein). This is typically achieved by adjusting the HMW PEG:label ratio, as would be known in the art. Given the relative size of the average molecule of HMW PEG, it is expected that a wide variety of labels will be suitable for attachment to HMW PEG with substantial preservation of the biological activity thereof.

Labels contemplated by the invention are those labels known in the art, which include a radiolabel, a chromophore, a fluorophore, and a reporter (including an enzyme that catalyzes the production of a detectable compound and a binding partner such as an antibody that localizes a detectable compound in the vicinity of the reporter). Exemplary enzyme reporters include an enzymatic component of a luminescence system and a catalyst of a colorimetric reaction. More particularly, exemplary reporter molecules include biotin, avidin, streptavidin, and enzymes (e.g., horseradish peroxidase, luciferase, alkaline phosphatases, including secreted alkaline phosphatase (SEAP); β-galactosidase; β-glucuronidase; chloramphenicol acetyltransferase). The use of such reporters is well known to those of skill in the art and is described in, e.g., U.S. Pat. No. 3,817,837, U.S. Pat. No. 3,850,752, U.S. Pat. No. 3,996,345, and U.S. Pat. No. 4,277,437. Exemplary enzyme substrates, which may be converted to detectable compounds by reporter enzymes, include 5-bromo-4-chloro-3-indolyl β-D-galactopyranoside or Xgal, and Bluo-gal. Enzyme substrates, as compounds capable of conversion to detectable compounds, may also be labels in certain embodiments, as would be understood in the art. U.S. patents teaching labels, and their uses, include U.S. Pat. No. 3,817,837; U.S. Pat. No. 3,850,752; U.S. Pat. No. 3,939,350 and U.S. Pat. No. 3,996,345. Exemplary radiolabels are $^3$H, $^{14}$C, $^{32}$P, $^{33}$P, $^{35}$S, and $^{125}$I; exemplary fluorophores are fluorescein (FITC), rhodamine, Cy3, Cy5, aequorin, and green fluorescent protein. A preferred label is a fluorophore such as fluorescein.

The monitoring methods of the invention may also involve more than one label. In one embodiment, one label serves to identify the location of the HMW PEG following or during treatment, while a second label is specific for one or more microbes insofar as the label detectably associates with at least one microbe. For example, a monitoring method may include fluorescein attached to HMW PEG in a manner that substantially preserves the biological activity of the HMW PEG, and free (i.e., unattached) Xgal or bluo-gal for detection of prokaryote-specific β-galactosidase activity. The fluorescein localizes the HMW PEG, while a colored (blue) product indicates the presence of a lactose-metabolizing prokaryotic microbe, such as a Pseudomonad. The invention also includes monitoring methods wherein a single label provides this information (i.e., the location of HMW PEG and an indication of the presence of a microbe).

Any detection technique known in the art may be used in the monitoring methods of the invention. Several factors will influence the detection technique chosen, including the type of label, the biomaterial subjected to monitoring (e.g., epidermal cells of the skin, ear canal, or intestine; stool, mucus or tissue samples), the level of discrimination desired, whether quantitation is expected, and the like. Suitable detection techniques include simple visual inspection with the unaided eye, visual inspection with an instrument such as an endoscope, optionally equipped with a suitable light source and/or camera for recordation, the conventional use of Geiger counters, x-ray film, scintillation counters, and the like, and any other detection technique known in the art.

One of skill will recognize that the monitoring methods of the invention are useful in optimizing the treatment methods. For example, a monitoring method may be used to optimize the quantity and/or concentration of HMW PEG (e.g., to achieve a desired viscosity for a solution or mixture of HMW PEG), which is delivered to an epithelial cell, such as the epithelial cells of the ear canal to prevent or to treat swimmer's ear. By way of additional examples, optimization of bowel or intestinal treatments may be facilitated by endoscopic inspection of an intestinal tract exposed to labeled HMW PEG or by monitoring stool samples.

The monitoring methods of the invention include a stool assay for a microbe capable of adhering to an intestinal epithelial cell comprising contacting a microbe and an intestinal epithelial cell and detecting adherence of the microbe to the epithelial cell using any technique known in the art. In a preferred embodiment, the intestinal epithelial cell is immobilized on a suitable surface, such as the bottom and/or sides of a microtiter well. In another preferred embodiment, a direct label, or an indirect label such as a reporter capable of generating a detectable product, is added prior to, or during, the detecting step. The monitoring methods may further comprise addition of free label. For example, free Bluo-gal is added to a sample suspected of containing a lactose-metabolizing prokaryotic microbe; if present, the microbial enzyme β-galactosidase will cleave Bluo-gal to yield a detectable blue product.

In one embodiment, commercially available intestinal epithelial cells (e.g., Caco-2 cells, ATCC HTB 37, and/or IEC-6 cells, ATCC CRL 1952) are fixed to the wells of a microtiter dish using a conventional technique. A stool sample is collected and mixed with a fluid such as phosphate-buffered saline. The liquid phase of the mixture, containing suspended microbes, is obtained (e.g., by suitable filtration (i.e., separation of gross solids from bacteria in fluid suspension), decanting, or the like) and diluted 1:100 in PBS. Bluo-gal is added to the live microbial suspension. The microbial suspension is added to microtiter wells for 1 hour at 24° C., followed by washing of the wells with a suitable fluid (e.g., PBS) to remove unbound microbes. Microbes unbound and/or bound to the immobilized epithelial cells are detected, e.g., by counting using polarized light microscopy. In alternative embodiments, an immunoassay is used to detect adherence, with suitable immunological reagents being a microbe(s)-specific monoclonal or polyclonal antibody, optionally attached to a label such as a radiolabel, a fluorophore or a chromophore.

One of skill in the art will recognize that neither the intestinal epithelial cell nor the microbe is required to be immobilized, although such immobilization may facilitate accurate detection of microbes adhering to epithelial cells. For example, in one embodiment, an immobilized stool microbe is brought into contact with an intestinal epithelial cell that is not immobilized. Further, one of skill would recognize that any suitable fluid known in the art may be used to obtain the microbial suspension, with preferred fluids being any of the known isotonic buffers. Also, as noted above, any known label may be used to detect cell adherence.

In a related aspect, the invention provides a kit for assaying for microbial cell adherence comprising an epithelial cell and a protocol for assaying microbial cell adherence to the epithelial cell. The protocol describes a known method for detecting a microbe. A preferred kit includes an intestinal epithelial cell. Other kits of the invention further comprise a label, such as a fluorophore or a reporter.

Another monitoring method contemplated by the invention is an assay for microbial hydrophobicity. In this method, the relative or absolute hydrophobicity of a microbial cell is determined using any conventional technique. An exemplary technique involves exposure of any microbe to hydrophobic interaction chromatography, as would be known in the art. Ukuku et al., J. Food Prot. 65:1093-1099 (2002), incorporated herein by reference in its entirety. Another exemplary technique is non-polar:polar fluid partition (e.g., 1-octanol:water or xylene:water) of any microbe. See Majtan et al., Folia Microbiol (Praha) 47:445-449 (2002), incorporated herein by reference in its entirety.

In one embodiment of a hydrophobicity assay for monitoring PEG administration, a stool sample is suspended in 50 mM sodium phosphate buffer (pH 7.4) containing 0.15 M NaCl. Microbes in the suspension are collected by centrifugation and resuspended in the same buffer, and the centrifugation-resuspension cycle is repeated. If feasible, the microbes are resuspended in the same buffer to an absorbancy of 0.4 at 660 nm, which will permit monitoring spectrophotometrically, without using labeled PEG. The microbial suspension is treated with xylene (2.5:1, v/v, Merck), the suspension is vigorously mixed for two minutes, and the suspension is allowed to settle for 20 minutes at room temperature. The presence of microbes in the aqueous phase is then determined, for example by spectrophotometric determination of absorbancy at 660 nm. A blank containing the sodium phosphate buffer is used to eliminate background.

In obtaining microbial cells from stool samples for use in these methods, it is preferred that the HMW PEG be relatively insoluble in the fluid used to obtain the microbial suspension and any fluid used to dilute the microbial suspension.

The invention further provides a kit for performing the monitoring method comprising an assay for microbial hydrophobicity, which comprises an intestinal epithelial cell and a protocol describing the determination of microbial hydrophobicity. A preferred kit includes an intestinal epithelial cell. Related kits further comprise a label, such as a fluorophore or a reporter.

Still further, the invention provides a monitoring method comprising obtaining a sample of intestinal flora and detecting PA-I lectin/adhesin activity. Any technique for detecting PA-I lectin/adhesin activity known in the art may be used. For example, PA-I lectin/adhesin may be detected using an antibody (polyclonal, monoclonal, antibody fragment such as a Fab fragment, single chain, chimera, humanized or any other form of antibody known in the art) that specifically recognizes PA-I lectin/adhesin. The immunoassay takes the form of any immunoassay format known in the art, e.g., ELISA, Western, immunoprecipitation, and the like. Alternatively, one may detect a carbohydrate-binding capacity of PA-I lectin/adhesin or the intestinal epithelial barrier breaching activity of PA-I lectin/adhesin may be measured, e.g., by monitoring the trans-epithelial electrical resistance or TEER of an epithelial layer prior to, and/or during, exposure to a sample. In related kits, the invention provides a PA-I lectin/adhesin binding partner and a protocol for detecting PA-I lectin/adhesin activity (e.g., binding activity). Other kits according to the invention include any carbohydrate known to bind PA-I lectin/adhesin and a protocol for detecting PA-I lectin/adhesin activity (e.g., binding activity).

Numerous modifications and variations of the present invention are possible in view of the above teachings and are within the scope of the invention. The entire disclosures of all publications cited herein are hereby incorporated by reference.

What is claimed is:

1. A method of treating a microbe-mediated disorder in an animal, the microbe selected from the group consisting of *Escherichia coli*, *Clostridium, Pseudomonas aeruginosa, Enterobacteria cloacae, Serratia marcescens, Klebsiella oxytocia, Candida albicans, Candida globrata,* and *Bacillus anthracis*, the method comprising:

administering to the animal a composition comprising polyethylene glycol (PEG), wherein the PEG has an average molecular weight of at least 12,000 daltons and comprises a plurality of PEG molecules joined with a phenol linker, wherein the administering is oral or anal.

2. The method according to claim 1 wherein the PEG has an average molecular weight of at least 15,000 daltons.

3. The method according to claim 1 wherein the PEG has an average molecular weight of between about 15,000 and 20,000 daltons.

4. The method according to claim 1 wherein the PEG is in an aqueous solution comprising 5-20% PEG.

5. The method according to claim 4 wherein the aqueous solution comprises 10% PEG.

6. The method according to claim 1, wherein the composition further comprises a vehicle selected from the group consisting of a liquid solution, a topical gel, and a solution suitable for nebulizing.

7. The method according to claim 1 further comprising introducing an effective amount of a compound selected from the group consisting of dextran, dextran-coated L-glutamine and dextran-coated inulin into the intestine of the animal.

8. The method according to claim 1 further comprising introducing an effective amount of L-glutamine into the intestine of the animal.

9. The method according to claim 1 wherein the animal is selected from the group consisting of dog, cat, sheep, goat, cow, pig, chicken, horse and human.

10. The method according to claim 9 wherein the animal is human.

11. A method of treating an animal suffering from gut-derived sepsis, enteropathy, burn injury, severe neutropenia, swimmer's ear, acute otitis media, chronic otitis media, ventilator-associated pneumonia, necrotizing enterocolitis, antibiotic-induced diarrhea, pseudomembranous colitis, irritable bowel disease, neutropenic enterocolitis, neonatal enterocolitis, pancreatitis, chronic fatigue syndrome, dysbiosis syndrome, microscopic colitis, or a chronic urinary tract infection, the method comprising:

administering to the animal a composition comprising polyethylene glycol (PEG), wherein the PEG has an average molecular weight of at least 12,000 daltons and comprises a plurality of PEG molecules joined with a phenol linker, wherein the administering is oral or anal.

12. The method according to claim 11 wherein the PEG has an average molecular weight of at least 15,000 daltons.

13. The method according to claim 11 wherein the PEG has an average molecular weight of between about 15,000 and 20,000 daltons.

14. The method according to claim 11 wherein the PEG is in an aqueous solution comprising 5-20% PEG.

15. The method according to claim 14 wherein the aqueous solution comprises 10% PEG.

16. The method according to claim 11, wherein the composition further comprises a vehicle selected from the group consisting of a liquid solution, a topical gel, and a solution suitable for nebulizing.

17. The method according to claim 11 further comprising introducing an effective amount of a compound selected from the group consisting of dextran, dextran-coated L-glutamine and dextran-coated inulin into the intestine of the animal.

18. The method according to claim 11 further comprising introducing an effective amount of L-glutamine into the intestine of the animal.

19. The method according to claim 11 wherein the animal is selected from the group consisting of dog, cat, sheep, goat, cow, pig, chicken, horse and human.

20. The method according to claim 19 wherein the animal is human.

* * * * *

UNITED STATES PATENT AND TRADEMARK OFFICE
CERTIFICATE OF CORRECTION

PATENT NO.         : 9,549,946 B2                                Page 1 of 1
APPLICATION NO.    : 14/936088
DATED              : January 24, 2017
INVENTOR(S)        : John C. Alverdy It is certified that error appears in the above-identified patent and that said Letters Patent is hereby corrected as shown below:

In the Claims

At Column 29, Line 6, "globrata," should be -- glabrata, --.

At Column 30, Line 14, "15,000daltons." should be -- 15,000 daltons. --.

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 6

<210> SEQ ID NO 1
<211> LENGTH: 20
<212> TYPE: DNA
<213> ORGANISM: Artificial sequence
<220> FEATURE:
<223> OTHER INFORMATION: Synthetic primer

<400> SEQUENCE: 1
accctggaca ttattgggtg                                              20

<210> SEQ ID NO 2
<211> LENGTH: 20
<212> TYPE: DNA
<213> ORGANISM: Artificial sequence
<220> FEATURE:
<223> OTHER INFORMATION: Synthetic primer

<400> SEQUENCE: 2
cgatgtcatt accatcgtcg                                              20

<210> SEQ ID NO 3
<211> LENGTH: 20
<212> TYPE: DNA
<213> ORGANISM: Artificial sequence
<220> FEATURE:
<223> OTHER INFORMATION: Synthetic primer

<400> SEQUENCE: 3
ggacgggtga gtaatgccta                                              20

<210> SEQ ID NO 4
<211> LENGTH: 20
<212> TYPE: DNA
<213> ORGANISM: Artificial sequence
<220> FEATURE:
<223> OTHER INFORMATION: Synthetic primer

<400> SEQUENCE: 4
cgtaagggcc atgatgactt                                              20

<210> SEQ ID NO 5
<211> LENGTH: 27
<212> TYPE: DNA
<213> ORGANISM: Artificial sequence
<220> FEATURE:
<223> OTHER INFORMATION: Synthetic primer

<400> SEQUENCE: 5
tctagaacta gtggatcccc gcggatg                                      27

<210> SEQ ID NO 6
<211> LENGTH: 27
<212> TYPE: DNA
<213> ORGANISM: Artificial sequence
<220> FEATURE:
<223> OTHER INFORMATION: Synthetic primer

<400> SEQUENCE: 6
gcagactagg tcgacaagct tgatatc                                      27